US008791249B2

(12) United States Patent
Ng et al.

(10) Patent No.: US 8,791,249 B2
(45) Date of Patent: Jul. 29, 2014

(54) NUCLEIC ACID ENCODING HUMANIZED C-KIT ANTIBODY

(71) Applicant: Amgen Inc., Thousand Oaks, CA (US)

(72) Inventors: Gordon Ng, Vancouver (CA); Wenyan Shen, Wayne, PA (US)

(73) Assignee: Amgen Inc., Thousand Oaks, CA (US)

( * ) Notice: Subject to any disclaimer, the term of this patent is extended or adjusted under 35 U.S.C. 154(b) by 0 days.

(21) Appl. No.: 13/888,275

(22) Filed: May 6, 2013

(65) Prior Publication Data

US 2013/0288303 A1 Oct. 31, 2013

Related U.S. Application Data

(60) Division of application No. 13/046,463, filed on Mar. 11, 2011, now Pat. No. 8,436,150, which is a continuation of application No. 11/789,665, filed on Apr. 24, 2007, now Pat. No. 7,915,391.

(60) Provisional application No. 60/794,771, filed on Apr. 24, 2006.

(51) Int. Cl.
*C07H 21/04* (2006.01)
*C12N 15/00* (2006.01)
*C12P 21/06* (2006.01)

(52) U.S. Cl.
USPC .................. 536/23.53; 435/455; 435/69.1

(58) Field of Classification Search
CPC ..... A61K 38/00; A61K 45/06; C07D 471/04; C07D 401/14
See application file for complete search history.

(56) References Cited

U.S. PATENT DOCUMENTS

| | | | |
|---|---|---|---|
| 5,489,516 A | 2/1996 | Broudy et al. | |
| 5,545,533 A | 8/1996 | Bartke | |
| 5,624,821 A | 4/1997 | Winter | |
| 5,808,002 A | 9/1998 | Buhring | |
| 5,919,911 A | 7/1999 | Broudy et al. | |
| 7,144,731 B2 | 12/2006 | Zsabo | |
| 7,915,391 B2 | 3/2011 | Ng et al. | |
| 2007/0225293 A1 | 9/2007 | Moussy et al. | |

FOREIGN PATENT DOCUMENTS

| | | | |
|---|---|---|---|
| WO | WO 92/17505 A1 | 10/1992 | |
| WO | WO 01/87981 A1 | 11/2001 | |

OTHER PUBLICATIONS

Edwards, S.T. et al., "c-Kit immunophenotyping and metalloproteinase expression profiles of mast cells in interstitial lung diseases." Journal of Pathology. May 10, 2005. Vo 1, 206, pp. 279-290.
Raspollini, M.R. et al. "c-Kit expression resistance in ovarian carcinoma: an immunocytochemical study", Annals of Oncology. Apr. 2004. vol. 15. No. 4. pp. 594-597.
Wei, Z.R. et al. "Research progress of roles of inflammatory cells and cytokines in pulmonary fibrosis", Journal of Cellular and Molecular Immunology, 2005. No. 21 (suppl. 1). pp. 85-87.
Search Report/Office action dated Mar. 1, 2013, of corresponding Gulf Council Patent Application No. GCC/P/2007/8213.
Chaudhary, et al., "Pharmacologic differentiation of inflammation and fibrosis in the rat bleomycin model," American Journal of Respiratory and Critical Care Medicine vol. 173. pp. 769-776, (2006).
Lukacs, et al., "The role of stem cell factor (c-kit ligand) and inflammatory cytokines in pulmonary mast cell activation," Blood, 1996 87: 2262-2268.
Li, et al., "Mast cell, a promising therapeuic target in tubulointerstitial fibrosis," Medical Hypotheses, vol. 69 , Issue 1 , pp. 99-103, 2007.
Masuda, et al., "Mast cells play a partial role in allergen-induced subepithelial fibrosis in a murine model of allergic asthma," Clinical and experimental allergy, 2003, vol. 33, No. 5, 705-713.
Database Geneseq "Human antiFc epsilon RI alpha chain antibody #1," Database accession No. 11 AAW73873, 1999.
Database Geneseq "BHA10 VL#2 protein plus heavy constant domain of human IgG1 SeqID 62," Database accession No. ADJ11351, 2004.
Database Geneseq "Mouse sclerostin-specific antibody protein sequence," Database accession No. AEM19172, 2007.
Raspollini, et al., c-KIT expression and correlation with chemotherapy resistance in ovarian carcinoma: an immunocytochemical study, Annals of Oncology: Official Journal of the European Society for Medical Oncology, vol. 15, No. 4, Apr. 2004, pp. 594-597.
Written Opinion, PCT Searching Authority, issued Oct. 24, 2008, 7 pgs.
Hines, "Co-expression of c-kit and stem cell factor in breast cancer results in enhanced sensitivity to members of the EGF family of growth factors," Breast Cancer Research and Treatment, pp. 1-10, vol. 58, No. 1, 1999.
Ashman, et al,, "Epitope mapping and functional studies with three monoclonal antibodies to the c-kit receptor tyrosine kinase, YB5.B8, 17F11, and SR-1," Journal of Cellular Physiology, vol. 158, No. 3, Mar. 1994, pp. 545-554.
Methods in Molecular Biology, vol. 248: Antibody Engineering: Methods and Protocols, edited by B.K.C. Lo., Humana Press, Totowa, New Jersey, Dec. 5, 2003, pp. 135-159.
Rudikoff et al. PNAS 1982 79:1979.
Padlan et al. PNAS 1989, 86:5938-5942.
Bendig Methods: A Companion to Methods in Enzymology 1995; 8:83-93.
The Merck Manuals Online Medical Library, [Online], Whitehouse Station, NJ: Merck Research Laboratories, 2006-2007, [Retrieved on Jan. 19, 2009]. Retrieved from the Internet; <URL: http://www.merckmanuals.com/professional/print/sec19/ch278/ch278a.html.> Cystic Fibrosis, pp. 1-9.
Rader et al. (PNAS 1998, 95:8910-8915).
Broudy, et al., "Stem cell factor influences the proliferation and erythroid differentiation of the MB-02 . . . ," Blood, 1993 82:436-444.

*Primary Examiner* — Sharon Wen
(74) *Attorney, Agent, or Firm* — Charles K. Sholtz

(57) ABSTRACT

This invention relates to compositions and methods for treating c-Kit associated disorders such as fibrosis, and more particularly, to compositions containing humanized c-Kit antibodies.

6 Claims, 3 Drawing Sheets

SEQUENCE LISTING

<160> NUMBER OF SEQ ID NOS: 10

<210> SEQ ID NO 1
<211> LENGTH: 717
<212> TYPE: DNA
<213> ORGANISM: Homo sapiens

<400> SEQUENCE: 1

```
atggtgttgc agacccaggt cttcatttct ctgttgctct ggatctctgg tgcctacggg     60
gacatcgtga tgacccagtc tccagactcc ctggctgtgt ctctgggcga gagggccacc    120
atcaactgca gagccagtga aagtgttgat atttatggca atagttttat gcactggtac    180
cagcagaaac aggacagcc tcctaagctg ctcatttacc ttgcatccaa cctagaatct    240
ggggtccctg accgattcag tggcagcggg tctgggacag atttcactct caccatcagc    300
agcctgcagg ctgaagatgt ggcagtttat tactgtcagc aaaataatga ggatccgtac    360
acgttcggag gtgggaccaa ggtggaaata aaacgtacgg tggctgcacc atctgtcttc    420
atcttcccgc catctgatga gcagttgaaa tctggaactg cctctgttgt gtgcctgctg    480
aataacttct atcccagaga ggccaaagta cagtggaagg tggataacgc cctccaatcg    540
ggtaactccc aggagagtgt cacagagcag gacagcaagg acagcaccta cagcctcagc    600
agcaccctga cgctgagcaa agcagactac gagaaacaca aagtctacgc ctgcgaagtc    660
acccatcagg gcctgagctc gcccgtcaca aagagcttca caggggaga gtgttga      717
```

<210> SEQ ID NO 2
<211> LENGTH: 238
<212> TYPE: PRT
<213> ORGANISM: Homo sapiens

<400> SEQUENCE: 2

```
Met Val Leu Gln Thr Gln Val Phe Ile Ser Leu Leu Leu Trp Ile Ser
1               5                   10                  15

Gly Ala Tyr Gly Asp Ile Val Met Thr Gln Ser Pro Asp Ser Leu Ala
            20                  25                  30

Val Ser Leu Gly Glu Arg Ala Thr Ile Asn Cys Arg Ala Ser Glu Ser
        35                  40                  45

Val Asp Ile Tyr Gly Asn Ser Phe Met His Trp Tyr Gln Gln Lys Pro
    50                  55                  60

Gly Gln Pro Pro Lys Leu Leu Ile Tyr Leu Ala Ser Asn Leu Glu Ser
65                  70                  75                  80

Gly Val Pro Asp Arg Phe Ser Gly Ser Gly Ser Gly Thr Asp Phe Thr
                85                  90                  95

Leu Thr Ile Ser Ser Leu Gln Ala Glu Asp Val Ala Val Tyr Tyr Cys
            100                 105                 110

Gln Gln Asn Asn Glu Asp Pro Tyr Thr Phe Gly Gly Gly Thr Lys Val
        115                 120                 125

Glu Ile Lys Arg Thr Val Ala Ala Pro Ser Val Phe Ile Phe Pro Pro
    130                 135                 140
```

```
Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
225                 230                 235
```

<210> SEQ ID NO 3
<211> LENGTH: 1401
<212> TYPE: DNA
<213> ORGANISM: Homo sapiens

<400> SEQUENCE: 3

```
atggactgga cctggagggt cttctgcttg ctggcagtgg ccccaggtgc ccactcccag      60
gtgcagctgg tgcagtctgg ggctgaggtg aagaagcctg ggcctcagt gaaggtctcc     120
tgcaaggctt ctggatacac cttcaccagt tacaatatgc actgggtgcg ccaggcccct    180
ggacaagggc ttgagtggat gggagttatt tattcaggaa atggtgatac ttcctacaat    240
cagaagttca aggcagggt caccattacc gctgacaaat ccaccagcac agcctacatg     300
gagctgagca gcctgagatc tgaggacacg gccgtgtatt actgtgcgag agagagggat    360
actcgttttg gtaactgggg ccaagggact ctggtcaccg tctctagtgc ctccaccaag    420
ggcccatcgg tcttcccct ggcacccctcc tccaagagca cctctggggg cacagcggcc     480
ctgggctgcc tggtcaagga ctacttcccc gaaccggtga cggtgtcgtg gaactcaggc    540
gccctgacca gcggcgtgca caccttcccg gctgtcctac agtcctcagg actctactcc    600
ctcagcagcg tggtgaccgt gccctccagc agcttgggca cccagaccta catctgcaac    660
gtgaatcaca agcccagcaa caccaaggtg gacaagaaag ttgagcccaa atcttgtgac    720
aaaactcaca catgcccacc gtgcccagca cctgaactcc tggggggacc gtcagtcttc    780
ctcttccccc caaaacccaa ggacaccctc atgatctccc ggacccctga ggtcacatgc    840
gtggtggtgg acgtgagcca cgaagaccct gaggtcaagt tcaactggta cgtggacggc    900
gtggaggtgc ataatgccaa gacaaagccg cgggaggagc agtaccagag cacgtaccgt    960
gtggtcagcg tcctcaccgt cctgcaccag gactggctga atggcaagga gtacaagtgc   1020
aaggtctcca acaaagccct cccagccccc atcgagaaaa ccatctccaa agccaaaggg   1080
cagccccgag aaccacaggt gtacaccctg cccccatccc gggatgagct gaccaagaac   1140
caggtcagcc tgacctgcct ggtcaaaggc ttctatccca gcgacatcgc cgtggagtgg   1200
gagagcaatg ggcagccgga gaacaactac aagaccacgc ctcccgtgct ggactccgac   1260
ggctccttct tcctctatag caagctcacc gtggacaaga gcaggtggca gcaggggaac   1320
gtcttctcat gctccgtgat gcatgaggct ctgcacaacc actacacgca gaagagcctc   1380
tccctgtctc cgggtaaatg a                                             1401
```

<210> SEQ ID NO 4
<211> LENGTH: 466
<212> TYPE: PRT
<213> ORGANISM: Homo sapiens

<400> SEQUENCE: 4

```
Met Asp Trp Thr Trp Arg Val Phe Cys Leu Leu Ala Val Ala Pro Gly
1               5                   10                  15

Ala His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Ser Tyr Asn Met His Trp Val Arg Gln Ala Pro Gly Gln Gly Leu
    50                  55                  60

Glu Trp Met Gly Val Ile Tyr Ser Gly Asn Gly Asp Thr Ser Tyr Asn
65                  70                  75                  80

Gln Lys Phe Lys Gly Arg Val Thr Ile Thr Ala Asp Lys Ser Thr Ser
                85                  90                  95

Thr Ala Tyr Met Glu Leu Ser Ser Leu Arg Ser Glu Asp Thr Ala Val
            100                 105                 110

Tyr Tyr Cys Ala Arg Glu Arg Asp Thr Arg Phe Gly Asn Trp Gly Gln
        115                 120                 125

Gly Thr Leu Val Thr Val Ser Ser Ala Ser Thr Lys Gly Pro Ser Val
130                 135                 140

Phe Pro Leu Ala Pro Ser Ser Lys Ser Thr Ser Gly Gly Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
            180                 185                 190

Leu Gln Ser Ser Gly Leu Tyr Ser Leu Ser Ser Val Val Thr Val Pro
        195                 200                 205

Ser Ser Ser Leu Gly Thr Gln Thr Tyr Ile Cys Asn Val Asn His Lys
    210                 215                 220

Pro Ser Asn Thr Lys Val Asp Lys Lys Val Glu Pro Lys Ser Cys Asp
225                 230                 235                 240

Lys Thr His Thr Cys Pro Pro Cys Pro Ala Pro Glu Leu Leu Gly Gly
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser His Glu
        275                 280                 285

Asp Pro Glu Val Lys Phe Asn Trp Tyr Val Asp Gly Val Glu Val His
    290                 295                 300

Asn Ala Lys Thr Lys Pro Arg Glu Glu Gln Tyr Gln Ser Thr Tyr Arg
305                 310                 315                 320

Val Val Ser Val Leu Thr Val Leu His Gln Asp Trp Leu Asn Gly Lys
                325                 330                 335

Glu Tyr Lys Cys Lys Val Ser Asn Lys Ala Leu Pro Ala Pro Ile Glu
            340                 345                 350

Lys Thr Ile Ser Lys Ala Lys Gly Gln Pro Arg Glu Pro Gln Val Tyr
        355                 360                 365

Thr Leu Pro Pro Ser Arg Asp Glu Leu Thr Lys Asn Gln Val Ser Leu
    370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val
```

405                 410                 415
Leu Asp Ser Asp Gly Ser Phe Phe Leu Tyr Ser Lys Leu Thr Val Asp
            420                 425                 430

Lys Ser Arg Trp Gln Gln Gly Asn Val Phe Ser Cys Ser Val Met His
        435                 440                 445

Glu Ala Leu His Asn His Tyr Thr Gln Lys Ser Leu Ser Leu Ser Pro
    450                 455                 460

Gly Lys
465

<210> SEQ ID NO 5
<211> LENGTH: 1389
<212> TYPE: DNA
<213> ORGANISM: Homo sapiens

<400> SEQUENCE: 5
atggactgga cctggagggt cttctgcttg ctggcagtgg ccccaggtgc ccactcccag      60
gtgcagctgg tgcagtctgg ggctgaggtg aagaagcctg ggcctcagt gaaggtctcc     120 tgcaaggctt ctggatacac cttcaccagt acaatatgc actgggtgcg ccaggcccct     180
ggacaagggc ttgagtggat gggagttatt tattcaggaa atggtgatac ttcctacaat     240
cagaagttca aggcagggt caccattacc gctgacaaat ccaccagcac agcctacatg     300
gagctgagca gcctgagatc tgaggacacg gccgtgtatt actgtgcgag agagggat     360 actcgttttg gtaactgggg ccaagggact ctggtcaccg tctctagtgc ctccaccaag     420
ggcccatcgg tcttccccct ggcgccctgc tccaggagca cctccgagag cacagcggcc     480
ctgggctgcc tggtcaagga ctacttcccc gaaccggtga cggtgtcgtg gaactcaggc     540
gctctgacca gcggcgtgca caccttccca gctgtcctac agtcctcagg actctactcc     600
ctcagcagcg tggtgaccgt gccctccagc aacttcggca cccagaccta cacctgcaac     660
gtagatcaca agcccagcaa caccaaggtg gacaagacag ttgagcgcaa atgttgtgtc     720
gagtgcccac cgtgcccagc accacctgtg gcaggaccgt cagtcttcct cttccccca      780 aaacccaagg acaccctcat gatctcccgg acccctgagg tcacgtgcgt ggtggtggac     840
gtgagccacg aagaccccga ggtccagttc aactggtacg tggacggcgt ggaggtgcat     900
aatgccaaga caaagccacg ggaggagcag ttcaacagca cgttccgtgt ggtcagcgtc     960
ctcaccgttg tgcaccagga ctggctgaac ggcaaggagt acaagtgcaa ggtctccaac    1020
aaaggcctcc cagcccccat cgagaaaacc atctccaaaa ccaaagggca gccccgagaa    1080
ccacaggtgt acaccctgcc cccatcccgg gaggagatga ccaagaacca ggtcagcctg    1140
acctgcctgg tcaaaggctt ctaccccagc gacatcgccg tggagtggga gagcaatggg    1200
cagccggaga acaactacaa gaccacacct cccatgctgg actccgacgg ctccttcttc    1260
ctctacagca agctcaccgt ggacaagagc aggtggcagc aggggaacgt cttctcatgc    1320
tccgtgatgc atgaggctct gcacaaccac tacacgcaga gagcctctc cctgtctccg    1380 ggtaaatga                                                            1389

<210> SEQ ID NO 6
<211> LENGTH: 462
<212> TYPE: PRT
<213> ORGANISM: Homo sapiens

<400> SEQUENCE: 6

Met Asp Trp Thr Trp Arg Val Phe Cys Leu Leu Ala Val Ala Pro Gly

-continued

```
1               5                   10                  15
Ala His Ser Gln Val Gln Leu Val Gln Ser Gly Ala Glu Val Lys Lys
                20                  25                  30
Pro Gly Ala Ser Val Lys Val Ser Cys Lys Ala Ser Gly Tyr Thr Phe
                35                  40                  45
Thr Ser Tyr Asn Met His Trp Val Arg Gln Ala Pro Gly Gln Gly Leu
                50                  55                  60
Glu Trp Met Gly Val Ile Tyr Ser Gly Asn Gly Asp Thr Ser Tyr Asn
 65                 70                  75                  80
Gln Lys Phe Lys Gly Arg Val Thr Ile Thr Ala Asp Lys Ser Thr Ser
                85                  90                  95
Thr Ala Tyr Met Glu Leu Ser Ser Leu Arg Ser Glu Asp Thr Ala Val
                100                 105                 110
Tyr Tyr Cys Ala Arg Glu Arg Asp Thr Arg Phe Gly Asn Trp Gly Gln
                115                 120                 125
Gly Thr Leu Val Thr Val Ser Ser Ala Ser Thr Lys Gly Pro Ser Val
                130                 135                 140
Phe Pro Leu Ala Pro Cys Ser Arg Ser Thr Ser Glu Ser Thr Ala Ala
145                 150                 155                 160
Leu Gly Cys Leu Val Lys Asp Tyr Phe Pro Glu Pro Val Thr Val Ser
                165                 170                 175
Trp Asn Ser Gly Ala Leu Thr Ser Gly Val His Thr Phe Pro Ala Val
                180                 185                 190
Leu Gln Ser Ser Gly Leu Tyr Ser Leu Ser Ser Val Val Thr Val Pro
                195                 200                 205
Ser Ser Asn Phe Gly Thr Gln Thr Tyr Thr Cys Asn Val Asp His Lys
                210                 215                 220
Pro Ser Asn Thr Lys Val Asp Lys Thr Val Glu Arg Lys Cys Cys Val
225                 230                 235                 240
Glu Cys Pro Pro Cys Pro Ala Pro Pro Val Ala Gly Pro Ser Val Phe
                245                 250                 255
Leu Phe Pro Pro Lys Pro Lys Asp Thr Leu Met Ile Ser Arg Thr Pro
                260                 265                 270
Glu Val Thr Cys Val Val Val Asp Val Ser His Glu Asp Pro Glu Val
                275                 280                 285
Gln Phe Asn Trp Tyr Val Asp Gly Val Glu Val His Asn Ala Lys Thr
                290                 295                 300
Lys Pro Arg Glu Glu Gln Phe Asn Ser Thr Phe Arg Val Val Ser Val
305                 310                 315                 320
Leu Thr Val Val His Gln Asp Trp Leu Asn Gly Lys Glu Tyr Lys Cys
                325                 330                 335
Lys Val Ser Asn Lys Gly Leu Pro Ala Pro Ile Glu Lys Thr Ile Ser
                340                 345                 350
Lys Thr Lys Gly Gln Pro Arg Glu Pro Gln Val Tyr Thr Leu Pro Pro
                355                 360                 365
Ser Arg Glu Glu Met Thr Lys Asn Gln Val Ser Leu Thr Cys Leu Val
                370                 375                 380
Lys Gly Phe Tyr Pro Ser Asp Ile Ala Val Glu Trp Glu Ser Asn Gly
385                 390                 395                 400
Gln Pro Glu Asn Asn Tyr Lys Thr Thr Pro Pro Met Leu Asp Ser Asp
                405                 410                 415
Gly Ser Phe Phe Leu Tyr Ser Lys Leu Thr Val Asp Lys Ser Arg Trp
                420                 425                 430
```

Gln Gln Gly Asn Val Phe Ser Cys Ser Val Met His Glu Ala Leu His
        435                 440                 445

Asn His Tyr Thr Gln Lys Ser Leu Ser Leu Ser Pro Gly Lys
        450                 455                 460

<210> SEQ ID NO 7
<211> LENGTH: 717
<212> TYPE: DNA
<213> ORGANISM: Homo sapiens

<400> SEQUENCE: 7
atggagacag acacactcct gctatgggtg ctgctgctct gggttccagg ttccacaggt       60
aacattgtgt tgacccaatc tccagcttct ttggctgtgt ctctagggct gagggccacc     120
atatcctgca gagccagtga aagtgttgat atttatggca atagttttat gcactggtac     180
cagcagaaac caggacagcc acccaaactc ctcatctatc ttgcatccaa cctagaatct     240
ggggtccctg ccaggttcag tggcagtggg tctaggacag acttcaccct caccattgat     300
cctgtggagg ctgatgatgc tgcaacctat tactgtcagc aaaataatga ggatccgtac     360
acgttcggag gggggaccaa gctggaaata aaacgggctg atgctgcacc aactgtatcc     420
atcttcccac catccagtga gcagttaaca tctggaggtg cctcagtcgt gtgcttcttg     480
aacaacttct accccaaaga catcaatgtc aagtggaaga ttgatggcag tgaacgacaa     540
aatggcgtcc tgaacagttg gactgatcag gacagcaaag acagcaccta cagcatgagc     600
agcaccctca cgttgaccaa ggacgagtat gaacgacata cagctatac ctgtgaggcc      660 actcacaaga catcaacttc acccattgtc aagagcttca caggaatga gtgttga        717

<210> SEQ ID NO 8
<211> LENGTH: 238
<212> TYPE: PRT
<213> ORGANISM: Homo sapiens

<400> SEQUENCE: 8

Met Glu Thr Asp Thr Leu Leu Leu Trp Val Leu Leu Leu Trp Val Pro
1               5                   10                  15

Gly Ser Thr Gly Asn Ile Val Leu Thr Gln Ser Pro Ala Ser Leu Ala
            20                  25                  30

Val Ser Leu Gly Leu Arg Ala Thr Ile Ser Cys Arg Ala Ser Glu Ser
        35                  40                  45

Val Asp Ile Tyr Gly Asn Ser Phe Met His Trp Tyr Gln Gln Lys Pro
    50                  55                  60

Gly Gln Pro Pro Lys Leu Leu Ile Tyr Leu Ala Ser Asn Leu Glu Ser
65                  70                  75                  80

Gly Val Pro Ala Arg Phe Ser Gly Ser Gly Ser Arg Thr Asp Phe Thr
                85                  90                  95

Leu Thr Ile Asp Pro Val Glu Ala Asp Asp Ala Thr Tyr Tyr Cys
            100                 105                 110

Gln Gln Asn Asn Glu Asp Pro Tyr Thr Phe Gly Gly Gly Thr Lys Leu
        115                 120                 125

Glu Ile Lys Arg Ala Asp Ala Ala Pro Thr Val Ser Ile Phe Pro Pro
    130                 135                 140

Ser Ser Glu Gln Leu Thr Ser Gly Gly Ala Ser Val Val Cys Phe Leu
145                 150                 155                 160

Asn Asn Phe Tyr Pro Lys Asp Ile Asn Val Lys Trp Lys Ile Asp Gly
                165                 170                 175

```
Ser Glu Arg Gln Asn Gly Val Leu Asn Ser Trp Thr Asp Gln Asp Ser
            180                 185                 190

Lys Asp Ser Thr Tyr Ser Met Ser Ser Thr Leu Thr Leu Thr Lys Asp
        195                 200                 205

Glu Tyr Glu Arg His Asn Ser Tyr Thr Cys Glu Ala Thr His Lys Thr
    210                 215                 220

Ser Thr Ser Pro Ile Val Lys Ser Phe Asn Arg Asn Glu Cys
225                 230                 235
```

<210> SEQ ID NO 9
<211> LENGTH: 1401
<212> TYPE: DNA
<213> ORGANISM: Homo sapiens

<400> SEQUENCE: 9

```
atgggatgga gttgtatcat cctcttcttg gtagcaacag ctacaggtgt ccactcccag      60
gtgcaactgc agcagcctgg ggctgagctg gtgaagcctg ggcctcagt gaagatgtcc     120
tgcaaggctt ctggctacac atttaccagt tacaatatgc actgggtaaa gcagacacct     180
ggacagggcc tggaatggat tggagttatt tattcaggaa atggtgatac ttcctacaat     240
cagaagttca aggcaaggc cacattgact gcagacaaat cctccagcac agcctacatg     300
caaatcaaca gcctgacatc tgaggactct gcggtctatt actgtgcaag agagggat     360
actcgttttg gtaactgggg ccaagggact ctggtcactg tctctgcagc caaaacaaca     420
gccccatcgg tctatccact ggcccctgtg tgtggagata caactggctc ctcggtgact     480
ctaggatgcc tggtcaaggg ttatttccct gagccagtga ccttgacctg gaactctgga     540
tccctgtcca gtggtgtgca caccttccca gctgtcctgc agtctgacct ctacaccctc     600
agcagctcag tgactgtaac ctcgagcacc tggcccagcc agtccatcac ctgcaatgtg     660
gcccaccccgg caagcagcac caaggtggac aagaaaattg agcccagagg gcccacaatc     720
aagccctgtc ctccatgcaa atgcccagca cctaacctct gggtggacc atccgtcttc     780
atcttccctc caaagatcaa ggatgtactc atgatctccc tgagccccat agtcacatgt     840
gtggtggtgg atgtgagcga ggatgaccca gatgtccaga tcagctggtt tgtgaacaac     900
gtggaagtac acacagctca gacacaaacc catagagagg attacaacag tactctccgg     960
gtggtcagtg ccctccccat ccagcaccag gactggatga gtggcaagga gttcaaatgc    1020
aaggtcaaca acaaagacct cccagcgccc atcgagagaa ccatctcaaa acccaaaggg    1080
tcagtaagag ctccacaggt atatgtcttg cctccaccag aagaagagat gactaagaaa    1140
caggtcactc tgacctgcat ggtcacagac ttcatgcctg aagacattta cgtggagtgg    1200
accaacaacg gaaaacagag ctaaactac aagaacactg aaccagtcct ggactctgat    1260
ggttcttact tcatgtacag caagctgaga gtggaaaaga gaactgggt ggaaagaaat    1320
agctactcct gttcagtggt ccacgagggt ctgcacaatc accacacgac taagagcttc    1380
tcccggactc cgggtaaatg a                                              1401
```

<210> SEQ ID NO 10
<211> LENGTH: 466
<212> TYPE: PRT
<213> ORGANISM: Homo sapiens

<400> SEQUENCE: 10

```
Met Gly Trp Ser Cys Ile Ile Leu Phe Leu Val Ala Thr Ala Thr Gly
1               5                   10                  15
```

```
Val His Ser Gln Val Gln Leu Gln Gln Pro Gly Ala Glu Leu Val Lys
            20                  25                  30

Pro Gly Ala Ser Val Lys Met Ser Cys Lys Ala Ser Gly Tyr Thr Phe
        35                  40                  45

Thr Ser Tyr Asn Met His Trp Val Lys Gln Thr Pro Gly Gln Gly Leu
    50                  55                  60

Glu Trp Ile Gly Val Ile Tyr Ser Gly Asn Gly Asp Thr Ser Tyr Asn
65                  70                  75                  80

Gln Lys Phe Lys Gly Lys Ala Thr Leu Thr Ala Asp Lys Ser Ser Ser
                85                  90                  95

Thr Ala Tyr Met Gln Ile Asn Ser Leu Thr Ser Glu Asp Ser Ala Val
            100                 105                 110

Tyr Tyr Cys Ala Arg Glu Arg Asp Thr Arg Phe Gly Asn Trp Gly Gln
        115                 120                 125

Gly Thr Leu Val Thr Val Ser Ala Ala Lys Thr Thr Ala Pro Ser Val
    130                 135                 140

Tyr Pro Leu Ala Pro Val Cys Gly Asp Thr Thr Gly Ser Ser Val Thr
145                 150                 155                 160

Leu Gly Cys Leu Val Lys Gly Tyr Phe Pro Glu Pro Val Thr Leu Thr
                165                 170                 175

Trp Asn Ser Gly Ser Leu Ser Ser Gly Val His Thr Phe Pro Ala Val
            180                 185                 190

Leu Gln Ser Asp Leu Tyr Thr Leu Ser Ser Ser Val Thr Val Thr Ser
        195                 200                 205

Ser Thr Trp Pro Ser Gln Ser Ile Thr Cys Asn Val Ala His Pro Ala
    210                 215                 220

Ser Ser Thr Lys Val Asp Lys Lys Ile Glu Pro Arg Gly Pro Thr Ile
225                 230                 235                 240

Lys Pro Cys Pro Pro Cys Lys Cys Pro Ala Pro Asn Leu Leu Gly Gly
                245                 250                 255

Pro Ser Val Phe Ile Phe Pro Pro Lys Ile Lys Asp Val Leu Met Ile
            260                 265                 270

Ser Leu Ser Pro Ile Val Thr Cys Val Val Asp Val Ser Glu Asp
        275                 280                 285

Asp Pro Asp Val Gln Ile Ser Trp Phe Val Asn Asn Val Glu Val His
        290                 295                 300

Thr Ala Gln Thr Gln Thr His Arg Glu Asp Tyr Asn Ser Thr Leu Arg
305                 310                 315                 320

Val Val Ser Ala Leu Pro Ile Gln His Gln Asp Trp Met Ser Gly Lys
                325                 330                 335

Glu Phe Lys Cys Lys Val Asn Asn Lys Asp Leu Pro Ala Pro Ile Glu
            340                 345                 350

Arg Thr Ile Ser Lys Pro Lys Gly Ser Val Arg Ala Pro Gln Val Tyr
        355                 360                 365

Val Leu Pro Pro Pro Glu Glu Glu Met Thr Lys Lys Gln Val Thr Leu
    370                 375                 380

Thr Cys Met Val Thr Asp Phe Met Pro Glu Asp Ile Tyr Val Glu Trp
385                 390                 395                 400

Thr Asn Asn Gly Lys Thr Glu Leu Asn Tyr Lys Asn Thr Glu Pro Val
                405                 410                 415

Leu Asp Ser Asp Gly Ser Tyr Phe Met Tyr Ser Lys Leu Arg Val Glu
            420                 425                 430
```

```
Lys Lys Asn Trp Val Glu Arg Asn Ser Tyr Ser Cys Ser Val Val His
        435                 440                 445

Glu Gly Leu His Asn His His Thr Thr Lys Ser Phe Ser Arg Thr Pro
    450                 455                 460

Gly Lys
465
```

NUCLEIC ACID ENCODING HUMANIZED C-KIT ANTIBODY

This application is a divisional application of U.S. patent application Ser. No. 13/046,463 filed Mar. 11, 2011, which is a continuation application of U.S. Pat. No. 7,915,391 issued Mar. 21, 2011, which claims the benefit of U.S. Provisional Application No. 60/794,771, filed Apr. 24, 2006. The disclosures of all these applications are hereby incorporated by reference in their entireties herein.

TECHNICAL FIELD

This invention relates to compositions for treating c-Kit associated inflammatory, fibrotic, autoimmune and cancerous diseases and to compositions containing humanized c-Kit antibodies.

BACKGROUND OF THE INVENTION

Mast cells have been implicated in the mediation of inflammatory conditions such as asthma, rheumatoid arthritis and inflammatory bowel disease and the role in allergic inflammation is widely recognized. Mast cells are increased in number in lung explants from severe asthmatics and are the major source of clinically relevant inflammatory mediators such as leukotriences, histamine and Th2 cytokines. Mast cells are the major source of pre-formed TNF in disease tissues.

Stem Cell Factor (SCF) is a glycoprotein that signals through the cell and membrane associated tyrosine kinase receptor hereafter defined as c-Kit, and this signaling pathway plays a key role in hematopoiesis acting both as a positive and negative regulator, often in synergy with other cytokines. A soluble shed c-Kit receptor may play a role in regulating SCF. C-Kit is expressed on pluripotent hematopoietic stem cells which are the precurors to mature cells belonging to lymphoid and erythroid lineages. Unlike other hematopoietic cells, mast cell precursors and mature mast cells retain high-levels of c-Kit expression. Hence SCF signaling via c-Kit is vital for mast cell development, function, trafficking and survival. It also plays a role in gametogenesis, and melanogenesis. Mice with inactivating c-Kit mutations in the W locus have virtually no mast cells. Activating c-Kit mutations in man are associated with mastocytosis.

c-Kit positive pluripotent hematopoietic stem cells are precursors to multiple cell types including mesenchymal cells, fibroblasts and mast cells. Fibrotic disease is characterized in part by excessive fibroblast activity and proliferation resulting in the extracellular matrix deposition. C-Kit positive bone marrow pluripotent hematopoietic stem cells have been reported to be a source of the fibroblasts and mast cells in fibrotic tissues.

Mast cells can provide a sustained source of inflammatory, angiogenic, mitogenic and fibrogenic mediators. Mast cells are functionally and anatomically coupled to fibroblasts and have a direct role in activating fibroblasts. Mast cells increase the kinetics and magnitude of fibroblast mediated collagen contraction, extracellular matrix deposition and can transform fibroblasts into myofibroblasts. Fibroblasts in turn secrete SCF to further activate and expand mast cells, and both cell types are components of the fibrogenic network.

Mast cell number and mast cell mediators are significantly elevated in most human fibrotic diseases including idiopathic pulmonary fibrosis (IPF) and Scleroderma. Differential mast cell phenotypes are detected in some scleroderma patients and in the Tsk mouse model of scleroderma. An aggressive systemic form of mastocytosis may be characterized by myelofibrosis indicating that mast cells can be effector cells in fibrosis.

Gleevec™ and others in the class like Sutent™ are multi-targeted tyrosine kinase receptor inhibitors that can target c-Kit signaling activity, but inhibit a number of other kinases. These kinase inhibitors are indicated for the oncology setting. Myelosuppression, anemia and a number of side-effects including cardiotoxicity and peripheral edema have been reported for Gleevec. Therefore these molecules may not possess the best benefit to risk profile for chronic treatment of diseases associated with c-Kit signaling. Thus, there is a need for new therapies and reagents, particularly those that are more potent and selective, and possess better safety profiles for the treatment of c-Kit associated inflammatory and fibrotic diseases. Such a compound could also show significantly better efficacy and safety profiles in oncologic diseases such as myeloid derived leukemia, diseases associated with c-Kit mutations such as GIST and mastocytosis, diseases associated with over-expression of c-kit and/or excessive SCF autocrine activity as in melanoma and various SCLCs. Therapies and reagents targeting human c-Kit and capable of affecting a therapeutic benefit without significant adverse effects are currently lacking.

SUMMARY OF THE INVENTION

The invention provides agents that are antagonists and neutral antagonists of SCF at the cell-associated and membrane c-Kit receptor, such as monoclonal antibodies. In a more specific embodiment, humanized (non-murine) monoclonal antibodies that bind c-Kit are provided. In yet more specific embodiments, the humanized antibodies of the invention comprise an amino acid sequence selected from those set forth in SEQ ID NOs 2, 4, and 6. The invention also provides nucleic acids encoding any of the preceding antibodies or specific binding agents. In a related embodiment of the invention, a vector comprising any of the aforementioned nucleic acid sequences is provided. In still another embodiment, a host cell is provided comprising any of the aforementioned nucleic acids or vectors.

In one embodiment, c-Kit binding agents and neutral antagonists may comprise an amino acid sequence of SEQ ID NO: 2, 4 or 6. In another embodiment, any of the aforementioned agents comprise an amino acid sequence that is at least 80%, 81%, 82%, 83%, 84%, 85%, 86%, 87%, 88%, 89%, 90%, 91%, 92%, 93%, 94%, 95%, 96%, 97%, 98%, 99% or more identical to one or more of the amino acid sequences set forth in SEQ ID NO: 2, 4 or 6. In such embodiments, the sequence variation relative to SEQ ID NO: 2, 4 or 6, respectively, may represent, for example, a conservative substitution of the corresponding framework region of an IgG using an alternative human amino acid at that position.

In exemplary embodiments, the antibody or specific binding agent that binds c-Kit comprises an amino acid sequence set forth in SEQ ID NO: 2, 4, or 6. However, it is contemplated that the antibodies of the invention may be a mixture of IgG antibody isotypes (for example, a mixture of the IgG1, IgG2, IgG3 or IgG4 subtypes).

Any of the aforementioned antibodies may be, e.g., a native or mutated IgG antibody (for example of the IgG1 or IgG3 subtype, or any other IgG subtype). The aforementioned antibodies can exhibit an avidity characterized by a $k_d$ of lower than $1\times10^{-2}$, or lower than $1\times10^{-3}$, or $1\times10^{-4}$, $1\times10^{-5}$, $1\times10^{-6}$, $1\times10^{-7}$, $1\times10^{-8}$, or $1\times10^{-9}$, as determined by surface plasmon resonance (BIAcore analysis).

The aforementioned antibodies can exhibit a neutral antagonist IC50 of lower than $1\times10^{-2}$, or lower than $1\times10^{-3}$, or $1\times10^{-4}$, $1\times10^{-5}$, $1\times10^{-6}$, $1\times10^{-7}$, $1\times10^{-8}$, or $1\times10^{-9}$, as determined by cellular assays. In a particular embodiment, the affinity and functional potency of the humanized antibody is at least comparable to the affinity and potency of a parent murine antibody. In a preferred embodiment, the humanized antibody is not an agonist of the c-Kit receptor and does not activate mast cells which could lead to anaphylactoid reactions and should exhibit a PD/PK and immunogenicity profile that is at least comparable to the parent murine antibody.

Numerous methods are contemplated in the present invention. For example, a method of producing an aforementioned antibody or specific binding agent is provided comprising culturing the aforementioned host cell such that the nucleic acid is expressed to produce the antibody or agent. Such methods may also comprise the step of recovering the antibody or agent from the host cell culture. In a related embodiment, an isolated antibody or agent produced by the aforementioned method is provided.

The invention further provides methods of using any of the preceding antibodies or specific binding agents, for example, to treat or prevent a c-Kit associated disorder by administering an effective amount thereof. One example of such disorder to be treated is a fibrotic disease.

DETAILED DESCRIPTION

Figure 1:
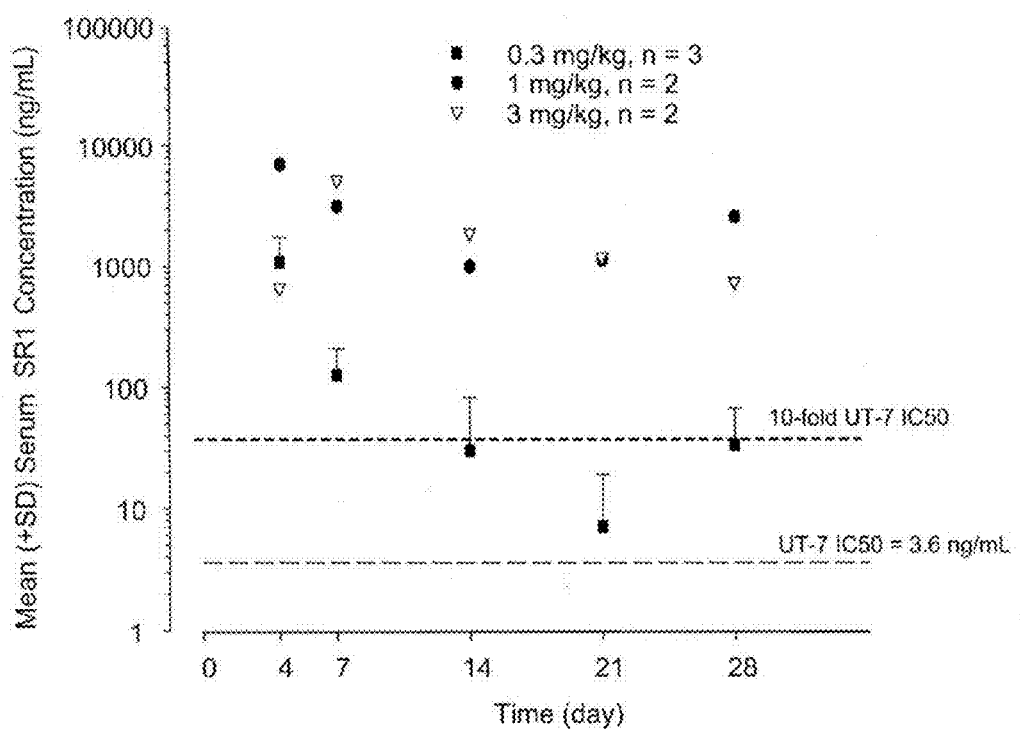
FIG. 1: SR-1 inhibits mast cells in wound activated model.
Figure 1:
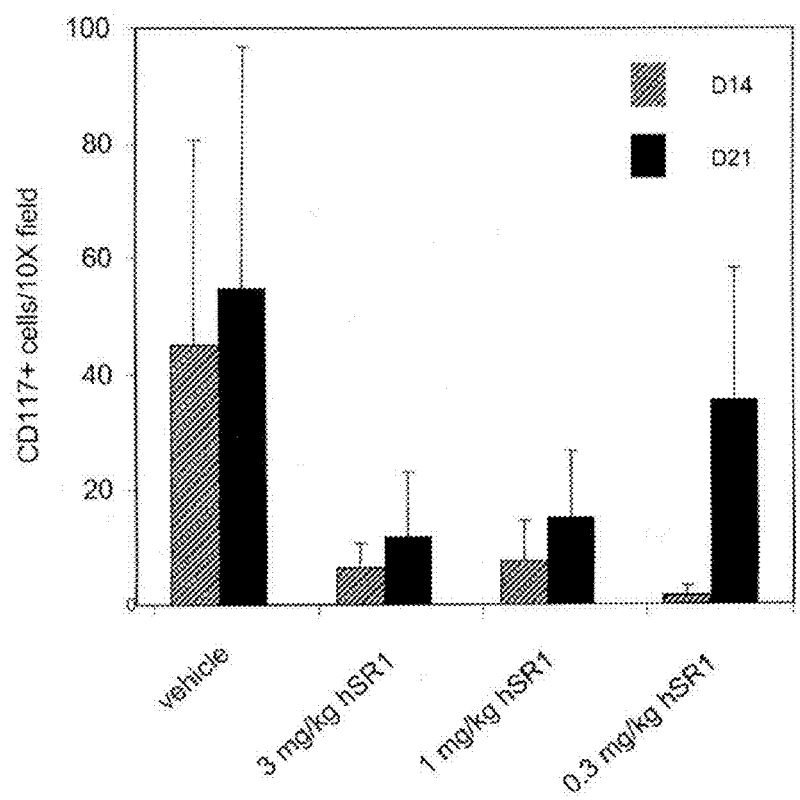

The murine anti-human c-Kit antibody SR-1 is described in U.S. Pat. Nos. 5,919,911, and 5,489,516, each of which are incorporated herein by reference. SR-1 showed suitable binding properties to c-kit and blocked SCF-mediated receptor signaling, however this molecule did not possess all the characteristics that would be desired in a human therapeutic beyond the obvious immunogenicity issues. Broudy reported that SR-1 possessed some agonist-like activity that could lead to receptor internalization and phosphorylation J Cell Physiol. 1994 March; 158(3):545-54. These functional activities render the molecule less efficacious and less safe. Though humanization of monoclonals is an established methodology and that biological activities are generally expected to be appropriately translated, the conformation of the humanized SR-1 antibody depending on the human framework may bring about different intrinsic activities at c-Kit and thus biological functions. In this particular example, the desired pharmacological properties but not the undesired "agonistic" properties would be sought, but the methodology to achieve this has not been published. The complementarity determining regions of the SR-1 antibody were inserted into a unique combination of the human heavy and light chains of structurally differing IgG1 and IgG2 and IgG4 while surprisingly maintaining similar affinity to c-Kit. However, each of these framework regions proved to have disadvantages.

The humanized SR-1 in the IgG2 background proved to have high affinity for c-Kit, but in multiple cell types was unable to fully block SCF-mediated receptor internalization and in cultured mast cell assays led to c-Kit phosphorylation, a survival signal, and mediated unusual clumping of the cells. These properties are potentially undesirable since the aim of a therapeutic strategy is to apoptotically deplete mast cells and precurors by blocking the survival SCF signal and to avoid mast cell activation that could lead to anaphylactoid reactions in vivo. When the mouse SR-1 CDR regions were inserted in the human IgG1 framework, affinity and functional potency were also maintained, but this background is less desirable due to the complement activation and cell mediated cytotoxicity often found with this isotype of antibody. When the mouse SR-1 CDR regions were inserted in the human IgG4 framework, affinity and functional potency were also maintained, but unexpectedly this molecule showed significant aggregation upon purification and scaleup.

Thus the present inventors sought to overcome the deficiencies in each of these molecules by creating an antibody that does not have complement activation, and does not activate c-kit and mast cells while retaining desired affinity, neutral antagonist potency for the membrane c-Kit receptor, and not the soluble c-Kit receptor. This antibody should also show appropriate PD/PK and is efficacious for depleting mast cells and without evidence of mast cell agonsim in vivo.

Humanized SR-1 Kappa Light Chain

Seq Id No: 1 represents the nucleic acid encoding the SR-1 humanized kappa light chain.

(SEQ ID NO: 1)

ATGGTGTTGCAGACCCAGGTCTTCATTTCTCTGTTGCTCTGGATCTCTG

GTGCCTACGGGGACATCGTGATGACCCAGTCTCCAGACTCCCTGGCTGT

GTCTCTGGGCGAGAGGGCCACCATCAACTGCAGAGCCAGTGAAAGTGTT

GATATTTATGGCAATAGTTTTATGCACTGGTACCAGCAGAAACCAGGAC

AGCCTCCTAAGCTGCTCATTTACCTTGCATCCAACCTAGAATCTGGGGT

CCCTGACCGATTCAGTGGCAGCGGGTCTGGGACAGATTTCACTCTCACC

ATCAGCAGCCTGCAGGCTGAAGATGTGGCAGTTTATTACTGTCAGCAAA

ATAATGAGGATCCGTACACGTTCGGAGGTGGGACCAAGGTGGAAATAAA

ACGTACGGTGGCTGCACCATCTGTCTTCATCTTCCCGCCATCTGATGAG

CAGTTGAAATCTGGAACTGCCTCTGTTGTGTGCCTGCTGAATAACTTCT

ATCCCAGAGAGGCCAAAGTACAGTGGAAGGTGGATAACGCCCTCCAATC

GGGTAACTCCCAGGAGAGTGTCACAGAGCAGGACAGCAAGGACAGCACC

TACAGCCTCAGCAGCACCCTGACGCTGAGCAAAGCAGACTACGAGAAAC

ACAAAGTCTACGCCTGCGAAGTCACCCATCAGGGCCTGAGCTCGCCCGT

CACAAAGAGCTTCAACAGGGGAGAGTGTTGA

Seq Id No: 2 is as follows where the bold face type represents the CDR's (e.g., CDR1 is amino acids 43 to 58 of SEQ ID NO: 2, CDR2 is amino acids 74 to 80 of SEQ ID NO: 2 and CDR3 is amino acids 113 to 121 of SEQ ID NO: 2):

```
                                                          (SEQ ID NO: 2)
  1  MVLQTQVFIS LLLWISGAYG DIVMTQSPDS LAVSLGERAT INCRASESVD

51  IYGNSFMHWY QQKPGQPPKL LIYLASNLES GVPDRFSGSG SGTDFTLTIS

101  SLQAEDVAVY YCQQNNEDPY TFGGGTKVEI KRTVAAPSVF IFPPSDEQLK

151  SGTASVVCLL NNFYPREAKV QWKVDNALQS GNSQESVTEQ DSKDSTYSLS

201  STLTLSKADY EKHKVYACEV THQGLSSPVT KSFNRGEC.
```

A mature humanized kappa light chain is amino acids 20 to 248 of SEQ ID NO: 2.
Humanized SR-1 Aglyco-IgG1 Heavy Chain
Seq Id No: 3

```
                                                 (SEQ ID NO: 3)
ATGGACTGGACCTGGAGGGTCTTCTGCTTGCTGGCAGTGGCCCCAGGTG

CCCACTCCCAGGTGCAGCTGGTGCAGTCTGGGGCTGAGGTGAAGAAGCC

TGGGGCCTCAGTGAAGGTCTCCTGCAAGGCTTCTGGATACACCTTCACC

AGTTACAATATGCACTGGGTGCGCCAGGCCCCTGGACAAGGGCTTGAGT

GGATGGGAGTTATTTATTCAGGAAATGGTGATACTTCCTACAATCAGAA

GTTCAAAGGCAGGGTCACCATTACCGCTGACAAATCCACCAGCACAGCC

TACATGGAGCTGAGCAGCCTGAGATCTGAGGACACGGCCGTGTATTACT

GTGCGAGAGAGGGATACTCGTTTTGGTAACTGGGGCCAAGGGACTCT

GGTCACCGTCTCTAGTGCCTCCACCAAGGGCCCATCGGTCTTCCCCCTG

GCACCCTCCTCCAAGAGCACCTCTGGGGGCACAGCGGCCCTGGGCTGCC

TGGTCAAGGACTACTTCCCCGAACCGGTGACGGTGTCGTGGAACTCAGG

CGCCCTGACCAGCGGCGTGCACACCTTCCCGGCTGTCCTACAGTCCTCA

GGACTCTACTCCCTCAGCAGCGTGGTGACCGTGCCCTCCAGCAGCTTGG

GCACCCAGACCTACATCTGCAACGTGAATCACAAGCCCAGCAACACCAA
```

-continued
```
   GGTGGACAAGAAAGTTGAGCCCAAATCTTGTGACAAAACTCACACATGC

15 CCACCGTGCCCAGCACCTGAACTCCTGGGGGGACCGTCAGTCTTCCTCT

TCCCCCCAAAACCCAAGGACACCCTCATGATCTCCCGGACCCCTGAGGT

CACATGCGTGGTGGTGGACGTGAGCCACGAAGACCCTGAGGTCAAGTTC

20 AACTGGTACGTGGACGGCGTGGAGGTGCATAATGCCAAGACAAAGCCGC

GGGAGGAGCAGTACCAGAGCACGTACCGTGTGGTCAGCGTCCTCACCGT

CCTGCACCAGGACTGGCTGAATGGCAAGGAGTACAAGTGCAAGGTCTCC

25 AACAAAGCCCTCCCAGCCCCCATCGAGAAAACCATCTCCAAAGCCAAAG

GGCAGCCCCGAGAACCACAGGTGTACACCCTGCCCCCATCCCGGGATGA

GCTGACCAAGAACCAGGTCAGCCTGACCTGCCTGGTCAAAGGCTTCTAT

CCCAGCGACATCGCCGTGGAGTGGGAGAGCAATGGGCAGCCGGAGAACA

30 ACTACAAGACCACGCCTCCCGTGCTGGACTCCGACGGCTCCTTCTTCCT

CTATAGCAAGCTCACCGTGGACAAGAGCAGGTGGCAGCAGGGGAACGTC

TTCTCATGCTCCGTGATGCATGAGGCTCTGCACAACCACTACACGCAGA

35 AGAGCCTCTCCCTGTCTCCGGGTAAATGA.
```

The CDR's are represented in bold face type (e.g., CDR1 is amino acids 50 to 54 of SEQ ID NO: 4, CDR2 is amino acids 69 to 85 of SEQ ID NO: 4, and CDR 3 is amino acids 118 to 125 of SEQ ID NO: 4):

```
                                                 (Seq Id No: 4)
  1  MDWTWRVFCL LAVAPGAHSQ VQLVQSGAEV KKPGASVKVS CKASGYTFTS

51  YNMHWVRQAP GQGLEWMGVI YSGNGDTSYN QKFKGRVTIT ADKSTSTAYM

101  ELSSLRSEDT AVYYCARERD TRFGNWGQGT LVTVSSASTK GPSVFPLAPS

151  SKSTSGGTAA LGCLVKDYFP EPVTVSWNSG ALTSGVHTFP AVLQSSGLYS

201  LSSVVTVPSS SLGTQTYICN VNHKPSNTKV DKKVEPKSCD KTHTCPPCPA

251  PELLGGPSVF LFPPKPKDTL MISRTPEVTC VVVDVSHEDP EVKFNWYVDG

301  VEVHNAKTKP REEQYQSTYR VVSVLTVLHQ DWLNGKEYKC KVSNKALPAP

351  IEKTISKAKG QPREPQVYTL PPSRDELTKN QVSLTCLVKG FYPSDIAVEW

401  ESNGQPENNY KTTPPVLDSD GSFFLYSKLT VDKSRWQQGN VFSCSVMHEA

451  LHNHYTQKSL SLSPGK
```

Humanized SR-1 IgG2 Heavy Chain (Seq Id No: 5)
ATGGACTGGACCTGGAGGGTCTTCTGCTTGCTGGCAGTGGCCCCAGGTG
CCCACTCCCAGGTGCAGCTGGTGCAGTCTGGGGCTGAGGTGAAGAAGCC
TGGGGCCTCAGTGAAGGTCTCCTGCAAGGCTTCTGGATACACCTTCACC
AGTTACAATATGCACTGGGTGCGCCAGGCCCCTGGACAAGGGCTTGAGT -continued
GGATGGGAGTTATTTATTCAGGAAATGGTGATACTTCCTACAATCAGAA
GTTCAAAGGCAGGGTCACCATTACCGCTGACAAATCCACCAGCACAGCC
TACATGGAGCTGAGCAGCCTGAGATCTGAGGACACGGCCGTGTATTACT
GTGCGAGAGAGAGGGATACTCGTTTTGGTAACTGGGGCCAAGGGACTCT
GGTCACCGTCTCTAGTGCCTCCACCAAGGGCCCATCGGTCTTCCCCCTG
GCGCCCTGCTCCAGGAGCACCTCCGAGAGCACAGCGGCCCTGGGCTGCC
TGGTCAAGGACTACTTCCCCGAACCGGTGACGGTGTCGTGGAACTCAGG
CGCTCTGACCAGCGGCGTGCACACCTTCCCAGCTGTCCTACAGTCCTCA
GGACTCTACTCCCTCAGCAGCGTGGTGACCGTGCCCTCCAGCAACTTCG
GCACCCAGACCTACACCTGCAACGTAGATCACAAGCCCAGCAACACCAA
GGTGGACAAGACAGTTGAGCGCAAATGTTGTGTCGAGTGCCCACCGTGC
CCAGCACCACCTGTGGCAGGACCGTCAGTCTTCCTCTTCCCCCCAAAAC
CCAAGGACACCCTCATGATCTCCCGGACCCCTGAGGTCACGTGCGTGGT
GGTGGACGTGAGCCACGAAGACCCCGAGGTCCAGTTCAACTGGTACGTG
GACGGCGTGGAGGTGCATAATGCCAAGACAAAGCCACGGGAGGAGCAGT
TCAACAGCACGTTCCGTGTGGTCAGCGTCCTCACCGTTGTGCACCAGGA
CTGGCTGAACGGCAAGGAGTACAAGTGCAAGGTCTCCAACAAAGGCCTC
CCAGCCCCCATCGAGAAAACCATCTCCAAAACCAAAGGGCAGCCCCGAG
AACCACAGGTGTACACCCTGCCCCCATCCCGGGAGGAGATGACCAAGAA -continued
CCAGGTCAGCCTGACCTGCCTGGTCAAAGGCTTCTACCCCAGCGACATC
GCCGTGGAGTGGGAGAGCAATGGGCAGCCGGAGAACAACTACAAGACCA
CACCTCCCATGCTGGACTCCGACGGCTCCTTCTTCCTCTACAGCAAGCT
CACCGTGGACAAGAGCAGGTGGCAGCAGGGGAACGTCTTCTCATGCTCC
GTGATGCATGAGGCTCTGCACAACCACTACACGCAGAAGAGCCTCTCCC
TGTCTCCGGGTAAATGA

The following is the full length amino acid sequence of the SR-1 IgG2 heavy chain, and the CDR's are represented in bold face type:

(Seq Id No: 6)
```
  1 MDWTWRVFCL LAVAPGAHSQ VQLVQSGAEV KKPGASVKVS CKASGYTFTS
 51 YNMHWVRQAP GQGLEWMGVI YSGNGDTSYN QKFKGRVTIT ADKSTSTAYM
101 ELSSLRSEDT AVYYCARERD TRFGNWGQGT LVTVSSASTK GPSVFPLAPC
151 SRSTSESTAA LGCLVKDYFP EPVTVSWNSG ALTSGVHTFP AVLQSSGLYS
201 LSSVVTVPSS NFGTQTYTCN VDHKPSNTKV DKTVERKCCV ECPPCPAPPV
251 AGPSVFLFPP KPKDTLMISR TPEVTCVVVD VSHEDPEVQF NWYVDGVEVH
301 NAKTKPREEQ FNSTFRVVSV LTVVHQDWLN GKEYKCKVSN KGLPAPIEKT
351 ISKTKGQPRE PQVYTLPPSR EEMTKNQVSL TCLVKGFYPS DIAVEWESNG
401 QPENNYKTTP PMLDSDGSFF LYSKLTVDKS RWQQGNVFSC SVMHEALHNH
451 YTQKSLSLSP GK
```

SR-1 MULC (SEQ ID NO: 7)
ATGGAGACAGACACACTCCTGCTATGGGTGCTGCTGCTCTGGGTTCCAG
GTTCCACAGGTAACATTGTGTTGACCCAATCTCCAGCTTCTTTGGCTGT
GTCTCTAGGGCTGAGGGCCACCATATCCTGCAGAGCCAGTGAAAGTGTT
GATATTTATGGCAATAGTTTTATGCACTGGTACCAGCAGAAACCAGGAC
AGCCACCCAAACTCCTCATCTATCTTGCATCCAACCTAGAATCTGGGGT
CCCTGCCAGGTTCAGTGGCAGTGGGTCTAGGACAGACTTCACCCTCACC
ATTGATCCTGTGGAGGCTGATGATGCTGCAACCTATTACTGTCAGCAAA
ATAATGAGGATCCGTACACGTTCGGAGGGGGGACCAAGCTGGAAATAAA
ACGGGCTGATGCTGCACCAACTGTATCCATCTTCCCACCATCCAGTGAG
CAGTTAACATCTGGAGGTGCCTCAGTCGTGTGCTTCTTGAACAACTTCT
ACCCCAAAGACATCAATGTCAAGTGGAAGATTGATGGCAGTGAACGACA
AAATGGCGTCCTGAACAGTTGGACTGATCAGGACAGCAAAGACAGCACC
TACAGCATGAGCAGCACCCTCACGTTGACCAAGGACGAGTATGAACGAC
ATAACAGCTATACCTGTGAGGCCACTCACAAGACATCAACTTCACCCAT
TGTCAAGAGCTTCAACAGGAATGAGTGTTGA

The CDR's are represented in bold face type:

```
                                                              (Seq Id No: 8)
  1  METDTLLLWV LLLWVPGSTG NIVLTQSPAS LAVSLGLRAT ISCRASESVD
 51  IYGNSFMHWY QQKPGQPPKL LIYLASNLES GVPARFSGSG SRTDFTLTID
101  PVEADDAATY YCQQNNEDPY TFGGGTKLEI KRADAAPTVS IFPPSSEQLT
151  SGGASVVCFL NNFYPKDINV KWKIDGSERQ NGVLNSWTDQ DSKDSTYSMS
201  STLTLTKDEY ERHNSYTCEA THKTSTSPIV KSFNRNEC
```

SR-1 muIgG2a Heavy Chain

```
                                           (Seq Id No: 9)
ATGGGATGGAGTTGTATCATCCTCTTCTTGGTAGCAACAGCTACAGGTG
TCCACTCCCAGGTGCAACTGCAGCAGCCTGGGGCTGAGCTGGTGAAGCC
TGGGGCCTCAGTGAAGATGTCCTGCAAGGCTTCTGGCTACACATTTACC
AGTTACAATATGCACTGGGTAAAGCAGACACCTGGACAGGGCCTGGAAT
GGATTGGAGTTATTTATTCAGGAAATGGTGATACTTCCTACAATCAGAA
GTTCAAAGGCAAGGCCACATTGACTGCAGACAAATCCTCCAGCACAGCC
TACATGCAAATCAACAGCCTGACATCTGAGGACTCTGCGGTCTATTACT
GTGCAAGAGAGAGGGATACTCGTTTTGGTAACTGGGGCCAAGGGACTCT
GGTCACTGTCTCTGCAGCCAAAACAACAGCCCCATCGGTCTATCCACTG
GCCCCTGTGTGTGGAGATACAACTGGCTCCTCGGTGACTCTAGGATGCC
TGGTCAAGGGTTATTTCCCTGAGCCAGTGACCTTGACCTGGAACTCTGG
ATCCCTGTCCAGTGGTGTGCACACCTTCCCAGCTGTCCTGCAGTCTGAC
CTCTACACCCTCAGCAGCTCAGTGACTGTAACCTCGAGCACCTGGCCCA
GCCAGTCCATCACCTGCAATGTGGCCCACCCGGCAAGCAGCACCAAGGT
GGACAAGAAAATTGAGCCCAGAGGGCCCACAATCAAGCCCTGTCCTCCA
TGCAAATGCCCAGCACCTAACCTCTTGGGTGGACCATCCGTCTTCATCT
TCCCTCCAAAGATCAAGGATGTACTCATGATCTCCCTGAGCCCCATAGT
CACATGTGTGGTGGTGGATGTGAGCGAGGATGACCCAGATGTCCAGATC
AGCTGGTTTGTGAACAACGTGGAAGTACACACAGCTCAGACACAAACCC
ATAGAGAGGATTACAACAGTACTCTCCGGGTGGTCAGTGCCCTCCCCAT
CCAGCACCAGGACTGGATGAGTGGCAAGGAGTTCAAATGCAAGGTCAAC
AACAAAGACCTCCCAGCGCCCATCGAGAGAACCATCTCAAAACCCAAAG
GGTCAGTAAGAGCTCCACAGGTATATGTCTTGCCTCCACCAGAAGAAGA
GATGACTAAGAAACAGGTCACTCTGACCTGCATGGTCACAGACTTCATG
CCTGAAGACATTTACGTGGAGTGGACCAACAACGGGAAAACAGAGCTAA
ACTACAAGAACACTGAACCAGTCCTGGACTCTGATGGTTCTTACTTCAT
GTACAGCAAGCTGAGAGTGGAAAAGAAGAACTGGGTGGAAAGAAATAGC
TACTCctgttcagtggtccacgagggtctgcacaatcaccacacgacta
agagcttctccaggactccgggtaaatgA
```

```
                                                             (Seq Id No: 10)
  1  MGWSCIILFL VATATGVHSQ VQLQQPGAEL VKPGASVKMS CKASGYTFTS YNMHWVKQTP
 61  GQGLEWIGVI YSGNGDTSYN QKFKGKATLT ADKSSSTAYM QINSLTSEDS AVYYCARERD
121  TRFGNWGQGT LVTVSAAKTT APSVYPLAPV CGDTTGSSVT LGCLVKGYFP EPVTLTWNSG
181  SLSSGVHTFP AVLQSDLYTL SSSVTVTSST WPSQSITCNV AHPASSTKVD KKIEPRGPTI
241  KPCPPCKCPA PNLLGGPSVF IFPPKIKDVL MISLSPIVTC VVVDVSEDDP DVQISWFVNN
301  VEVHTAQTQT HREDYNSTLR VVSALPIQHQ DWMSGKEFKC VNNKDLPAP IERTISKPKG
361  SVRAPQVYVL PPPEEEMTKK QVTLTCMVTD FMPEDIYVEW TNNGKTELNY KNTEPVLDSD
421  GSYFMYSKLR VEKKNWVERN SYSCSVVHEG LHNHHTTKSF SRTPGK
```

The light chain CDR1 of SR-1 is RASESVDIYGNSFMH (amino acids 44 to 58 of SEQ ID NO: 8), CDR2 is LASNLES (amino acids 74 to 80 of SEQ ID NO: 8), and CDR3 is QQNNEDPYT, (amino acids 111 to 121 of SEQ ID NO: 8). Heavy chain CDR1 is SYNMH, (amino acids 50 to 54 of SEQ ID NO: 10), CDR2 is VIYSGNGDTSYNQKFKG, (amino acids 69 to 85 of SEQ ID NO: 10), CDR3 is RDTRFGN, (amino acids 118 to 125 of SEQ ID NO: 10).

It is understood that each of the heavy and light chains depicted in the present application are processed in the cell to a mature form. Accordingly, signal peptides are cleaved and in the case of heavy chains of antibodies, the C-terminal lysine is cleaved. Accordingly, the mature form is processed proteolytically and also includes other post translational modifications such as glycosylation if expressed in mammalian cells. The signal peptide for each heavy and light chain are amino acids 1 to 20 of SEQ ID NOs: 2 and 10, and amino acids 1 to 19 of SEQ ID NOs: 4, 6, and 10.

The nucleotide and amino acid sequences of the light chain of murine SR-1 are set forth in SEQ ID NO: 7 and SEQ ID NO: 8. The nucleotide and amino acid sequences of the heavy chain of murine SR-1 is set forth in SEQ ID NO: 9 and SEQ ID NO: 10. Variants with further substitutions (e.g. conservative substitutions of the murine amino acids) may also retain the high binding affinity. Substitutions, deletions or insertions in positions within the CDRs and framework may be made without affecting affinity.

In one embodiment, the humanized antibody comprises a light chain that retains the original murine CDRs of murine SR-1, e.g., positions about 44-58, about 74-80 and about 113-121 of SEQ ID NO: 8. In other embodiments the humanized antibody comprises a heavy chain that retains the murine CDRs of murine SR-1, e.g., positions about 50-54, about 68-85 and about 118-125 of SEQ ID NO: 10, and has a human derived framework region. As used herein, it is understood that the term "about" contemplates two to five amino acid position changes so long as the affinity to c-Kit is maintained.

In one embodiment, such agents may comprise an amino acid sequence set forth in SEQ ID NO: 2, 4, or 6. In another embodiment, any of the aforementioned agents comprise an amino acid sequence that is at least 80%, 81%, 82%, 83%, 84%, 85%, 86%, 87%, 88%, 89%, 90%, 91%, 92%, 93%, 94%, 95%, 96%, 97%, 98%, 99% or more identical to the amino acid sequence set forth in SEQ ID NO: 2, 4, or 6. In such embodiments, the sequence variation relative to SEQ ID NO: 2, 4, or 6, respectively, may represent, for example, a conservative substitution of the corresponding framework region of an IgG using an alternative human amino acid at that position.

In one embodiment, the aforementioned antibodies exhibit an avidity characterized by a $k_d$ of lower than $10^{-2}$, or lower than $10^{-3}$, or $10^{-4}$, $10^{-5}$, $10^{-6}$, $10^{-7}$, $10^{-8}$, $10^{-9}$, as determined by surface plasmon resonance (BIAcore analysis). In another embodiment the aforementioned antibodies exhibit a neutral antagonist potency IC50 lower than $1\times10^{-2}$, or lower than $1\times10^{-3}$, or $1\times10^{-4}$, $1\times10^{-5}$, $1\times10^{-6}$, $1\times10^{-7}$, $1\times10^{-8}$, $1\times10^{-9}$, as determined by cellular assays.

The present invention provides a variety of specific binding and neutral antagonist agents, including but not limited to human or humanized c-Kit specific antibodies, that are derived from murine SR-1 and retain desirable characteristics such as Kd (dissociation rate constant) for c-Kit in the range of $1\times10^{-2}$ or lower, or ranging down to $1\times10^{-9}$ or lower, (e.g., $10^{-2}$, $10^{-3}$, $10^{-4}$, $10^{-5}$, $10^{-6}$, $10^{-7}$, $10^{-8}$, $10^{-9}$ or lower) and/or neutral antagonist IC50 for c-Kit in the range of $1\times10^{-2}$ or lower, or ranging down to $1\times10^{-9}$ or lower, (e.g., $10^{-2}$, $10^{-3}$, $10^{-4}$, $10^{-5}$, $10^{-6}$, $10^{-7}$, $10^{-8}$, $10^{-9}$ or lower) and/or the ability to reduce symptoms of a c-Kit associated disorder. The invention also provides nucleic acids encoding such specific binding agent polypeptides, vectors and recombinant host cells comprising such nucleic acids, methods of producing such specific binding agents, pharmaceutical formulations including such specific binding agents, methods of preparing the pharmaceutical formulations, and methods of treating patients with the pharmaceutical formulations and compounds.

Nucleic acids encoding these modified light chain variable regions were constructed and co-expressed with nucleic acids encoding a CDR-grafted or a humanized heavy chain and vice versa, and optionally may be linked to constant regions. Any humanized or chimeric heavy chain and light chains may be combined as long as suitable binding affinity is maintained. The desired genes were introduced into mammalian cells and the resultant recombinant immunoglobulin products were expressed, purified and characterized.

The term "antibody" is used in the broadest sense and includes fully assembled antibodies, monoclonal antibodies (including human, humanized or chimeric antibodies), polyclonal antibodies, multispecific antibodies (e.g., bispecific antibodies), and antibody fragments that can bind antigen (e.g., Fab', F'(ab)$_2$, Fv, single chain antibodies, diabodies), comprising complementarity determining regions (CDRs) of the foregoing as long as they exhibit the desired biological activity. The term "antibody" explicitly excludes murine antibody (i.e. antibody produced by a murine hybridoma or having the same sequence as an antibody produced by a murine hybridoma) from the scope of the term.

The term "specific binding agent" includes antibodies as defined above and recombinant peptides or other compounds that contain sequences derived from CDRs having the desired antigen-binding properties. Specifically included in the term are peptides containing amino acid sequences that are at least 80%, 90% or 100% identical to one or more CDRs of murine SR-1, preferably including heavy chain CDR3.

As used herein, the term "neutral antagonist" is understood to mean a specific binding agent that is capable of inhibiting an agonists activity These agents includes antibodies as defined above and recombinant peptides or other compounds that contain sequences derived from CDRs having the desired antigen-binding properties. Specifically included in the term are peptides containing amino acid sequences that are at least 80%, 90% or 100% identical to one or more CDRs of murine SR-1, preferably including heavy chain CDR3.

Also included in the term are "peptibodies" which are molecules comprising an antibody Fc domain as the "vehicle" attached to at least one antigen-binding peptide. Antibody CDR's from the SR-1 antibody may be suitable for incorporation into a peptibody, particularly including the CDR3 of the heavy chain. The production of peptibodies is generally described in PCT publication WO 00/24782, published May 4, 2000. Peptides may be linked in tandem (i.e., sequentially), with or without linkers. Peptides containing a cysteinyl residue may be cross-linked with another Cys-containing peptide, either or both of which may be linked to a vehicle. Any peptide having more than one Cys residue may form an intrapeptide disulfide bond, as well. Any of these peptides may be derivatized, for example the carboxyl terminus may be capped with an amino group, cysteines may be capped, or amino acid residues may substituted by moieties other than amino acid residues (see, e.g., Bhatnagar et al., J. Med. Chem. 39: 3814-9 (1996), and Cuthbertson et al., J. Med. Chem. 40: 2876-82 (1997), which are incorporated by reference herein in their entirety). The peptide sequences may be optimized, analogous to affinity maturation for antibodies, or otherwise altered by alanine scanning or random or directed mutagenesis followed by screening to identify the best binders. Lowman, Ann. Rev. Biophys. Biomol. Struct. 26: 401-24 (1997).

Various molecules can be inserted into the specific binding agent structure, e.g., within the peptide portion itself or between the peptide and vehicle portions of the specific binding agents, while retaining the desired activity of specific binding agent. One can readily insert, for example, molecules such as an Fc domain or fragment thereof, polyethylene glycol or other related molecules such as dextran, a fatty acid, a lipid, a cholesterol group, a small carbohydrate, a peptide, a cyotoxic agent, a chemotherapeutic agent, a detectable moiety as described herein (including fluorescent agents, radiolabels such as radioisotopes), an oligosaccharide, oligonucleotide, a polynucleotide, interference (or other) RNA, enzymes, hormones, or the like. Other molecules suitable for insertion in this fashion will be appreciated by those skilled in the art, and are encompassed within the scope of the invention. This includes insertion of, for example, a desired molecule in between two consecutive amino acids, optionally joined by a suitable linker.

An "isolated" antibody is one that has been identified and separated from a component of the cell that expressed it. Contaminant components of the cell are materials that would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody, and most preferably more than 99% by weight, (2) to a degree sufficient to obtain at least 15 residues of N-terminal or internal amino acid sequence, or (3) to homogeneity by SDS-PAGE under reducing or nonreducing conditions using Coomassie blue or, preferably, silver stain. Isolated naturally occurring antibody includes the antibody in situ within recombinant cells since at least one component of the antibody's natural environment will not be present. Ordinarily, however, isolated antibody will be prepared by at least one purification step.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against an individual antigenic site or epitope, in contrast to polyclonal antibody preparations that typically include different antibodies directed against different epitopes.

Depending on the amino acid sequence of the constant domain of their heavy chains, human immunoglobulins can be assigned to different classes. There are five major classes, IgA, IgD, IgE, IgG and IgM, and several of these may be further divided into subclasses or isotypes, e.g. IgG1, IgG2, IgG3, IgG4, IgA1 and IgA2. The heavy-chain constant domains that correspond to the different classes of immunoglobulins are called alpha, delta, epsilon, gamma and mu respectively. The subunit structures and three-dimensional configurations of different classes of immunoglobulins are well known. Different isotypes have different effector functions; for example, IgG1 and IgG3 isotypes have ADCC activity.

The term "hypervariable" region refers to the amino acid residues of an antibody which are responsible for antigen-binding. The hypervariable region comprises amino acid residues from a complementarity determining region or CDR [i.e., residues 24-34 (L), 50-56 (L2) and 89-97 (L3) in the light chain variable domain and 31-35 (H1), 50-65 (H2) and 95-102 (H3) in the heavy chain variable domain as described by Kabat et al., Sequences of Proteins of Immunological Interest, 5$^{th}$ Ed. Public Health Service, National Institutes of Health, Bethesda, Md. (1991)]. Even a single CDR may recognize and bind antigen, although with a lower affinity than the entire antigen binding site containing all of the CDRs. It is understood that the CDR of an antibody may include additional or fewer sequences outside the specified limits above so long as the antibody retains it's ability to bind the target molecule.

An alternative definition of residues from a hypervariable "loop" is described by Chothia et al., *J. Mol. Biol.* 196: 901-917 (1987) as residues 26-32 (L1), 50-52 (L2) and 91-96 (L3) in the light chain variable domain and 26-32 (H1), 53-55 (H2) and 96-101 (H3) in the heavy chain variable domain.

"Framework" or FR residues are those variable region residues other than the hypervariable region residues.

"Antibody fragments" comprise a portion of an intact full length antibody, preferably the antigen binding or variable region of the intact antibody. Examples of antibody fragments include Fab, Fab', F(ab')2, and Fv fragments; diabodies; linear antibodies (Zapata et al., Protein Eng., 8(10):1057-1062 (1995)); single-chain antibody molecules; and multispecific antibodies formed from antibody fragments.

Papain digestion of antibodies produces two identical antigen-binding fragments, called "Fab" fragments, each with a single antigen-binding site, and a residual "Fc" fragment which contains the constant region. The Fab fragment contains all of the variable domain, as well as the constant domain of the light chain and the first constant domain ($C_H1$) of the heavy chain. The Fc fragment displays carbohydrates and is responsible for many antibody effector functions (such as binding complement and cell receptors), that distinguish one class of antibody from another.

Pepsin treatment yields an F(ab')2 fragment that has two "Single-chain Fv" or "sFv" antibody fragments comprising the $V_H$ and $V_L$ domains of antibody, wherein these domains are present in a single polypeptide chain. Fab fragments differ from Fab' fragments by the inclusion of a few additional residues at the carboxy terminus of the heavy chain $C_H1$ domain including one or more cysteines from the antibody hinge region. Preferably, the Fv polypeptide further comprises a polypeptide linker between the $V_H$ and $V_L$ domains that enables the Fv to form the desired structure for antigen binding. For a review of sFv see Pluckthun in The Pharmacology of Monoclonal Antibodies, vol. 113, Rosenburg and Moore eds., Springer-Verlag, New York, pp. 269-315 (1994).

"Fv" is the minimum antibody fragment that contains a complete antigen recognition and binding site. This region consists of a dimer of one heavy- and one light-chain variable domain in tight, non-covalent association. It is in this configuration that the three CDRs of each variable domain interact to define an antigen binding site on the surface of the $V_H$ $V_L$ dimer. Collectively, the six CDRs confer antigen-binding specificity to the antibody. However, a single variable domain (or half of an Fv comprising only three CDRs specific for an antigen) has the ability to recognize and bind antigen, although at a lower affinity than the entire binding site.

The term "diabodies" refers to small antibody fragments with two antigen-binding sites, which fragments comprise a heavy-chain variable domain ($V_H$) connected to a light-chain variable domain ($V_L$) in the same polypeptide chain ($V_H V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and 30 Hollinger et al., Proc. Natl. Acad. Sci. USA, 90:6444-6448 (1993).

Various techniques have been developed for the production of antibody fragments. Traditionally, these fragments were derived via proteolytic digestion of intact antibodies, but can also be produced directly by recombinant host cells. See, for example, Better et al., Science 240: 1041-1043 (1988); Skerra et al. Science 240: 1038-1041 (1988); Carter et al., Bio/Technology 10:163-167 (1992).

As provided herein, the compositions and methods of treating inflammatory, autoimmune, oncologic and fibrotic disorders may utilize one or more anti-c-Kit therapeutics used singularly or in combination with other therapeutics to achieve the desired effects. Exemplary anti-fibrotic agents suitable for use in accordance with the invention include cytokines wherein the cytokine is selected from transforming growth factor β (TGF-β), interleukin-4 (IL-4), interleukin-5 (IL-5), interleukin-9 (IL-9), interleukin-13(IL-13), granulocyte/macrophage-colony stimulating factor (GM-CSF), tumor necrosis factor alpha (TNF-α), interleukin-1 beta (IL-1β), connective tissue growth factor (CTGF), interleukin-6 (IL-6), oncostatin M (OSM), platelet derived growth factor (PDGF), monocyte chemotactic protein 1 (CCL2/MCP-1), and pulmonary and activation-regulated chemokine (CCL18/PARC).

Antibodies derived from SR-1 according to the present invention are preferably produced by recombinant DNA methodology using one of the antibody expression systems well known in the art (see, e.g., Harlow and Lane, Antibodies: A Laboratory Manual, Cold Spring Harbor Laboratory (1988)). Such antibodies are also preferably chimeric fusion proteins having immunoglobulin derived variable sequences and human constant regions, or more preferably are more human-like monoclonal antibodies (such as human or humanized antibodies) that comprise human antibody residues but preferably retain at least the CDRs of murine SR-1. In addition to intact, full-length molecules, the term "antibody" also refers to fragments thereof or multimers or aggregates of intact molecules and/or fragments that bind to c-Kit.

The phrase "humanized antibody" refers to an antibody derived from a non-human antibody, typically a mouse monoclonal antibody. Alternatively, a humanized antibody may be derived from a chimeric antibody that retains or substantially retains the antigen binding properties of the parental, non-human, antibody but which exhibits diminished immunogenicity as compared to the parental antibody when administered to humans. The phrase "chimeric antibody," as used herein, refers to an antibody containing sequence derived from two different antibodies (see, e.g., U.S. Pat. No. 4,816,567) which typically originate from different species. Most typically, chimeric antibodies comprise human and murine antibody fragments, generally human constant and mouse variable regions.

Recombinant Production of Antibodies

The amino acid sequence of an immunoglobulin of interest may be determined by direct protein sequencing, and suitable encoding nucleotide sequences can be designed according to a universal codon table.

Alternatively, DNA encoding the monoclonal antibodies may be isolated and sequenced from the hybridoma cells using conventional procedures (e.g., by using oligonucleotide probes that are capable of binding specifically to genes encoding the heavy and light chains of the monoclonal antibodies). Sequence determination will generally require isolation of at least a portion of the gene or cDNA of interest. Usually this requires cloning the DNA or, preferably, mRNA (i.e., cDNA) encoding the monoclonal antibodies. Cloning is carried out using standard techniques (see, e.g., Sambrook et al. (1989) Molecular Cloning: A Laboratory Guide, Vols 1-3, Cold Spring Harbor Press, which is incorporated herein by reference). For example, a cDNA library may be constructed by reverse transcription of polyA+ mRNA, preferably membrane-associated mRNA, and the library screened using probes specific for human immunoglobulin polypeptide gene sequences. In a preferred embodiment, however, the polymerase chain reaction (PCR) is used to amplify cDNAs (or portions of full-length cDNAs) encoding an immunoglobulin gene segment of interest (e.g., a light chain variable segment). The amplified sequences can be readily cloned into any suitable vector, e.g., expression vectors, minigene vectors, or phage display vectors. It will be appreciated that the particular method of cloning used is not critical, so long as it is possible to determine the sequence of some portion of the immunoglobulin polypeptide of interest.

As used herein, an "isolated" nucleic acid molecule or "isolated" nucleic acid sequence is a nucleic acid molecule that is either (1) identified and separated from at least one contaminant nucleic acid molecule with which it is ordinarily associated in the natural source of the nucleic acid or (2) cloned, amplified, tagged, or otherwise distinguished from background nucleic acids such that the sequence of the nucleic acid of interest can be determined. An isolated nucleic acid molecule is other than in the form or setting in which it is found in nature. However, an isolated nucleic acid molecule includes a nucleic acid molecule contained in cells that ordinarily express the antibody where, for example, the nucleic acid molecule is in a chromosomal location different from that of natural cells.

One source for RNA used for cloning and sequencing is a hybridoma produced by obtaining a B cell from the transgenic mouse and fusing the B cell to an immortal cell. An advantage of using hybridomas is that they can be easily screened, and a hybridoma that produces a human monoclonal antibody of interest selected. Alternatively, RNA can be isolated from B cells (or whole spleen) of the immunized animal. When sources other than hybridomas are used, it may be desirable to screen for sequences encoding immunoglobulins or immunoglobulin polypeptides with specific binding characteristics. One method for such screening is the use of phage display technology. Phage display is described in e.g., Dower et al., WO 91/17271, McCafferty et al., WO 92/01047, and Caton and Koprowski, Proc. Natl. Acad. Sci. USA, 87:6450-6454 (1990), each of which is incorporated herein by reference. In one embodiment using phage display technology, cDNA from an immunized transgenic mouse (e.g., total spleen cDNA) is isolated, the polymerase chain reaction is used to amplify a cDNA sequences that encode a portion of an immunoglobulin polypeptide, e.g., CDR regions, and the amplified sequences are inserted into a phage vector. cDNAs encoding peptides of interest, e.g., variable region peptides with desired binding characteristics, are identified by standard techniques such as panning.

The sequence of the amplified or cloned nucleic acid is then determined. Typically the sequence encoding an entire variable region of the immunoglobulin polypeptide is determined, however, it will sometimes be adequate to sequence only a portion of a variable region, for example, the CDR-encoding portion. Typically the portion sequenced will be at least 30 bases in length, more often bases coding for at least about one-third or at least about one-half of the length of the variable region will be sequenced.

Sequencing can be carried out on clones isolated from a cDNA library, or, when PCR is used, after subcloning the amplified sequence or by direct PCR sequencing of the amplified segment. Sequencing is carried out using standard techniques (see, e.g., Sambrook et al. (1989) Molecular Cloning: A Laboratory Guide, Vols 1-3, Cold Spring Harbor Press, and Sanger, F. et al. (1977) Proc. Natl. Acad. Sci. USA 74: 5463-5467, which is incorporated herein by reference). By comparing the sequence of the cloned nucleic acid with published sequences of human immunoglobulin genes and cDNAs, one of skill will readily be able to determine, depending on the region sequenced, (i) the germline segment usage of the hybridoma immunoglobulin polypeptide (including the isotype of the heavy chain) and (ii) the sequence of the heavy and light chain variable regions, including sequences resulting from N-region addition and the process of somatic mutation. One source of immunoglobulin gene sequence information is the National Center for Biotechnology Information, National Library of Medicine, National Institutes of Health, Bethesda, Md.

Once isolated, the DNA may be operably linked to expression control sequences or placed into expression vectors, which are then transfected into host cells such as E. coli cells, simian COS cells, Chinese hamster ovary (CHO) cells, or myeloma cells that do not otherwise produce immunoglobulin protein, to direct the synthesis of monoclonal antibodies in the recombinant host cells. Recombinant production of antibodies is well known in the art.

Expression control sequences refer to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is operably linked when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, operably linked means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

Cell, cell line, and cell culture are often used interchangeably and all such designations herein include progeny. Transformants and transformed cells include the primary subject cell and cultures derived therefrom without regard for the number of transfers. It is also understood that all progeny may not be precisely identical in DNA content, due to deliberate or inadvertent mutations. Mutant progeny that have the same function or biological activity as screened for in the originally transformed cell are included.

The invention also provides isolated nucleic acids encoding specific binding agents or antibodies of the invention, optionally operably linked to control sequences recognized by a host cell, vectors and host cells comprising the nucleic acids, and recombinant techniques for the production of the specific binding agents or antibodies, which may comprise culturing the host cell so that the nucleic acid is expressed and, optionally, recovering the specific binding agent or antibody from the host cell culture or culture medium.

Many vectors are known in the art. Vector components may include one or more of the following: a signal sequence (that may, for example, direct secretion of the specific binding agent or antibody), an origin of replication, one or more selective marker genes (that may, for example, confer antibiotic or other drug resistance, complement auxotrophic deficiencies, or supply critical nutrients not available in the media), an enhancer element, a promoter, and a transcription termination sequence, all of which are well known in the art.

Suitable host cells include prokaryote, yeast, or higher eukaryote cells described above. Suitable prokaryotes for this purpose include eubacteria, such as Gram-negative or Gram-positive organisms, for example, Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as Bacilli such as *B. subtilis* and *B. licheniformis, Pseudomonas*, and *Streptomyces*. In addition to prokaryotes, eukaryotic microbes such as filamentous fungi or yeast are suitable cloning or expression hosts for specific binding agent-encoding vectors. *Saccharomyces cerevisiae*, or common baker's yeast, is the most commonly used among lower eukaryotic host microorganisms. However, a number of other genera, species, and strains are commonly available and useful herein, such as *Pichia*, e.g. *P. pastoris, Schizosaccharomyces pombe; Kluyveromyces, Yarrowia; Candida; Trichoderma reesia; Neurospora crassa; Schwanniomyces* such as *Schwanniomyces occidentalis*; and filamentous fungi such as, e.g., *Neurospora, Penicillium, Tolypocladium*, and *Aspergillus* hosts such as *A. nidulans* and *A. niger*.

Suitable host cells for the expression of glycosylated specific binding agent or antibody are derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection of such cells are publicly available, e.g., the L-1 variant of *Autographa californica* NPV and the Bm-5 strain of *Bombyx mori* NPV.

However, interest has been greatest in vertebrate cells, and propagation of vertebrate cells in culture (tissue culture) has become routine procedure. Examples of useful mammalian host cell lines are Chinese hamster ovary cells, including CHOK1 cells (ATCC CCL61), DXB-11, DG-44, and Chinese hamster ovary cells/−DHFR (CHO, Urlaub et al., Proc. Natl. Acad. Sci. USA 77: 4216 (1980)); monkey kidney CV1 line transformed by SV40 (COS-7, ATCC CRL 1651); human embryonic kidney line (293 or 293 cells subcloned for growth in suspension culture, [Graham et al., *J. Gen Virol.* 36: 59 (1977)]; baby hamster kidney cells (BHK, ATCC CCL 10); mouse sertoli cells (TM4, Mather, Biol. Reprod. 23: 243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human hepatoma cells (Hep G2, HB 8065); mouse mammary tumor (MMT 060562, ATCC CCL51); TRI cells (Mather et al., Annals N.Y. Acad. Sci. 383: 44-68 (1982)); MRC 5 cells or FS4 cells.

Host cells are transformed or transfected with the above-described nucleic acids or vectors for specific binding agent or antibody production and cultured in conventional nutrient media modified as appropriate for inducing promoters, selecting transformants, or amplifying the genes encoding the desired sequences. In addition, novel vectors and transfected cell lines with multiple copies of transcription units separated by a selective marker are particularly useful and preferred for the expression of specific binding agents or antibodies.

The host cells used to produce the specific binding agent or antibody of this invention may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., Meth. Enz. 58: 44 (1979), Barnes et al., Anal. Biochem. 102: 255 (1980), U.S. Pat. Nos. 4,767,704; 4,657,866; 4,927,762; 4,560,655; or 5,122,469; WO90103430; WO 87/00195; or U.S. Pat. Re. No. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as Gentamycin™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan. The expression vectors, pDC323 and pDC324 as described in U.S. Patent Application No. 20030082735, containing the appropriate respective light chain and heavy chain pair were transfected into the CS9 host cell line.

Upon culturing the host cells, the specific binding agent or antibody can be produced intracellularly, in the periplasmic space, or directly secreted into the medium. If the specific binding agent or antibody is produced intracellularly, as a first step, the particulate debris, either host cells or lysed fragments, is removed, for example, by centrifugation or ultrafiltration.

The specific binding agent or antibody composition can be purified using, for example, hydroxylapatite chromatography, cation or anion exchange chromatography, or preferably affinity chromatography, using the antigen of interest or protein A or protein G as an affinity ligand. Protein A can be used to purify specific binding agents or antibodies that are based on human γ1, γ2, or γ4 heavy chains (Lindmark et al., *J. Immunol. Meth.* 62: 1-13 (1983)). Protein G is recommended for all mouse isotypes and for human γ3 (Guss et al., EMBO J. 5: 15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the specific binding agent or antibody comprises a $C_H3$ domain, the Bakerbond ABX™ resin (J. T. Baker, Phillipsburg, N.J.) is useful for purification. Other techniques for protein purification such as ethanol precipitation, Reverse Phase HPLC, chromatofocusing, SDS-PAGE, and ammonium sulfate precipitation are also possible depending on the specific binding agent or antibody to be recovered.

Chimeric and Humanized Antibodies

Chimeric monoclonal antibodies, in which the variable Ig domains of a rodent monoclonal antibody are fused to human constant Ig domains, can be generated using standard procedures known in the art (See Morrison, S. L., et al. (1984) Chimeric Human Antibody Molecules; Mouse Antigen Binding Domains with Human Constant Region Domains, Proc. Natl. Acad. Sci. USA 81, 6841-6855; and, Boulianne, G. L., et al, Nature 312, 643-646. (1984)). Although some chimeric monoclonal antibodies have proved less immunogenic in humans, the rodent variable Ig domains can still lead to a significant human anti-rodent response.

Humanized antibodies may be achieved by a variety of methods including, for example: (1) grafting the non-human complementarity determining regions (CDRs) onto a human framework and constant region (a process referred to in the art as humanizing through "CDR grafting"), or, alternatively, (2) transplanting the entire non-human variable domains, but "cloaking" them with a human-like surface by replacement of surface residues (a process referred to in the art as "veneering"). These methods are disclosed in, e.g., Jones et al., Nature 321:522 525 (1986); Morrison et al., Proc. Natl. Acad. Sci., U.S.A., 81:6851 6855 (1984); Morrison and Oi, Adv. Immunol., 44:65 92 (1988); Verhoeyer et al., Science 239: 1534 1536 (1988); Padlan, Molec. Immun. 28:489 498 (1991); Padlan, Molec. Immunol. 31(3):169 217 (1994); and Kettleborough, C. A. et al., Protein Eng. 4(7):773 83 (1991) each of which is incorporated herein by reference.

In particular, a rodent antibody on repeated in vivo administration in man either alone or as a conjugate will bring about an immune response in the recipient against the rodent antibody; the so-called HAMA response (Human Anti Mouse Antibody). The HAMA response may limit the effectiveness of the pharmaceutical if repeated dosing is required. The immunogenicity of the antibody may be reduced by chemical modification of the antibody with a hydrophilic polymer such as polyethylene glycol or by using the methods of genetic engineering to make the antibody binding structure more human like.

CDR grafting involves introducing one or more of the six CDRs from the mouse heavy and light chain variable Ig domains into the appropriate framework regions of a human variable Ig domain. This technique (Riechmann, L., et al., Nature 332, 323 (1988)), utilizes the conserved framework regions (FR1-FR4) as a scaffold to support the CDR loops which are the primary contacts with antigen. A significant disadvantage of CDR grafting, however, is that it can result in a humanized antibody that has a substantially lower binding affinity than the original mouse antibody, because amino acids of the framework regions can contribute to antigen binding, and because amino acids of the CDR loops can influence the association of the two variable Ig domains. Chimeric SR-1 antibodies did not show appropriate functional potency in cell based assays.

To maintain the affinity of the humanized monoclonal antibody, the CDR grafting technique can be improved by choosing human framework regions that most closely resemble the framework regions of the original mouse antibody, and by site-directed mutagenesis of single amino acids within the framework or CDRs aided by computer modeling of the antigen binding site (e.g., Co, M. S., et al. (1994), J. Immunol. 152, 2968-2976).

One method of humanizing antibodies comprises aligning the non-human heavy and light chain sequences to human heavy and light chain sequences, selecting and replacing the non-human framework with a human framework based on such alignment, molecular modeling to predict the conformation of the humanized sequence and comparing to the conformation of the parent antibody. This process is followed by repeated back mutation of residues in the CDR region which disturb the structure of the CDRs until the predicted conformation of the humanized sequence model closely approximates the conformation of the non-human CDRs of the parent non-human antibody. Such humanized antibodies may be further derivatized to facilitate uptake and clearance, e.g., via Ashwell receptors (See, e.g., U.S. Pat. Nos. 5,530,101 and 5,585,089).

A number of humanizations of mouse monoclonal antibodies by rational design have been reported (See, for example, 20020091240 published Jul. 11, 2002, WO 92/11018 and U.S. Pat. No. 5,693,762, U.S. Pat. No. 5,766,866. Human engineering of antibodies have also been described in, e.g., Studnicka et al. U.S. Pat. No. 5,766,886; Studnicka et al. Protein Engineering 7: 805-814 (1994).

Production of Antibody Variants

Amino acid sequence variants of the desired specific binding agent or antibody may be prepared by introducing appropriate nucleotide changes into the encoding DNA, or by peptide synthesis. Such variants include, for example, deletions and/or insertions and/or substitutions of residues within the amino acid sequences of the specific binding agents or antibodies. Any combination of deletion, insertion, and substitution is made to arrive at the final construct, provided that the final construct possesses the desired characteristics. The amino acid changes also may alter post-translational processes of the specific binding agent or humanized or variant antibody, such as changing the number or position of glycosylation sites.

Nucleic acid molecules encoding amino acid sequence variants of the specific binding agent or antibody are prepared by a variety of methods known in the art. Such methods include oligonucleotide-mediated (or site-directed) mutagenesis, PCR mutagenesis, and cassette mutagenesis of an earlier prepared variant or a non-variant version of the specific binding agent or antibody.

A useful method for identification of certain residues or regions of the specific binding agent or antibody that are preferred locations for mutagenesis is called "alanine scanning mutagenesis," as described by Cunningham and Wells Science, 244:1081-1085 (1989). Here, a residue or group of target residues are identified (e.g., charged residues such as arg, asp, his, lys, and glu) and replaced by a neutral or negatively charged amino acid (most preferably alanine or polyalanine) to affect the interaction of the amino acids with antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, ala scanning or random mutagenesis is conducted at the target codon or region and the expressed variants are screened for the desired activity.

Ordinarily, amino acid sequence variants of the specific binding agent or antibody will have an amino acid sequence having at least 60% amino acid sequence identity with the original specific binding agent or antibody (murine or humanized) amino acid sequences of either the heavy or the light chain, or at least 65%, or at least 70%, or at least 75% or at least 80% identity, more preferably at least 85% identity, even more preferably at least 90% identity, and most preferably at least 95% identity, including for example, 80%, 81%, 82%, 83%, 84%, 85%, 86%, 87%, 88%, 89%, 90%, 91%, 92%, 93%, 94%, 95%, 96%, 97%, 98%, 99%, and 100%. Identity or homology with respect to this sequence is defined herein as the percentage of amino acid residues in the candidate sequence that are identical with the original sequence, after aligning the sequences and introducing gaps, if necessary, to achieve the maximum percent sequence identity, and not considering any conservative substitutions (as defined in Table I below) as part of the sequence identity. None of N-terminal, C-terminal, or internal extensions, deletions, or insertions into the specific binding agent or antibody sequence shall be construed as affecting sequence identity or homology. Thus, sequence identity can be determined by standard methods that are commonly used to compare the similarity in position of the amino acids of two polypeptides. Using a computer program such as BLAST or FASTA, two polypeptides are aligned for optimal matching of their respective amino acids (either along the full length of one or both sequences, or along a pre-determined portion of one or both sequences). The programs provide a default opening penalty and a default gap penalty, and a scoring matrix such as PAM 250 [a standard scoring matrix; see Dayhoff et al., in *Atlas of Protein Sequence and Structure*, vol. 5, supp. 3 (1978)] can be used in conjunction with the computer program. For example, the percent identity can then be calculated as: the total number of identical matches multiplied by 100 and then divided by the sum of the length of the longer sequence within the matched span and the number of gaps introduced into the longer sequences in order to align the two sequences.

Insertions

Amino acid sequence insertions include amino- and/or carboxyl-terminal fusions ranging in length from one residue to polypeptides containing a hundred or more residues, as well as intra-sequence insertions of single or multiple amino acid residues. Examples of terminal insertions include a specific binding agent or antibody with an N-terminal methionyl residue or the specific binding agent or antibody (including antibody fragment) fused to an epitope tag or a salvage receptor epitope. Other insertional variants of the specific binding agent or antibody molecule include the fusion to a polypeptide which increases the serum half-life of the specific binding agent or antibody, e.g. at the N-terminus or C-terminus.

Examples of epitope tags include the flu HA tag polypeptide and its antibody 12CA5 [Field et al., *Mol. Cell. Biol.* 8: 2159-2165 (1988)]; the c-myc tag and the 8F9, 3C7, 6E10, G4, B7 and 9E10 antibodies thereto [Evan et al., *Mol. Cell. Biol.* 5(12): 3610-3616 (1985)]; and the Herpes Simplex virus glycoprotein D (gD) tag and its antibody [Paborsky et al., *Protein Engineering* 3(6): 547-553 (1990)]. Other exemplary tags are a poly-histidine sequence, generally around six histidine residues, that permits isolation of a compound so labeled using nickel chelation. Other labels and tags, such as the FLAG® tag (Eastman Kodak, Rochester, N.Y.) are well known and routinely used in the art.

The term "salvage receptor binding epitope" refers to an epitope of the Fc region of an IgG molecule (e.g., $IgG_1$, $IgG_2$, $IgG_3$, or $IgG_4$) that is responsible for increasing the in vivo serum half-life of the IgG molecule.

Substitutions

Another type of variant is an amino acid substitution variant. These variants have at least one amino acid residue in the specific binding agent or antibody molecule removed and a different residue inserted in its place. Substitutional mutagenesis within any of the hypervariable or CDR regions or framework regions is contemplated. Conservative substitutions are shown in Table 1. The most conservative substitution is found under the heading of "preferred substitutions". If such substitutions result in no change in biological activity, then more substantial changes, denominated "exemplary substitutions" in Table 1, or as further described below in reference to amino acid classes, may be introduced and the products screened.

TABLE 1

| Original | Exemplary | Preferred Residue Substitutions |
|---|---|---|
| Ala (A) | val; leu; ile | val |
| Arg (R) | lys; gln; asn | lys |
| Asn (N) | gln; his; asp, lys; gln | arg |
| Asp (D) | glu; asn | glu |
| Cys (C) | ser; ala | ser |
| Gln (Q) | asn; glu | asn |
| Glu (E) | asp; gln | asp |
| Gly (G) | ala | |
| His (H) | asn; gln; lys; arg | |
| Ile (I) | leu; val; met; ala; phe; | leu norleucine |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala; tyr | |
| Pro (P) | ala | |
| Ser (S) | thr | |
| Thr (T) | ser | ser |
| Trp (W) | tyr; phe | tyr |
| Tyr (Y) | trp; phe; thr; ser | phe |
| Val (V) | ile; leu; met; phe; ala; norleucine | leu |

Substantial modifications in the biological properties of the specific binding agent or antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:

(1) hydrophobic: norleucine, met, ala, val, leu, ile;
(2) neutral hydrophilic: cys, ser, thr;
(3) acidic: asp, glu;
(4) basic: asn, gin, his, lys, arg;
(5) residues that influence chain orientation: gly, pro; and
(6) aromatic: trp, tyr, phe.

Conservative substitutions involve replacing an amino acid with another member of its class. Non-conservative substitutions involve replacing a member of one of these classes with a member of another class.

Any cysteine residue not involved in maintaining the proper conformation of the specific binding agent or humanized or variant antibody also may be substituted, generally with serine, to improve the oxidative stability of the molecule and prevent aberrant crosslinking. Conversely, cysteine bond(s) may be added to the specific binding agent or antibody to improve its stability (particularly where the antibody is an antibody fragment such as an Fv fragment).

Affinity Maturation

Affinity maturation involves preparing and screening specific binding agent or antibody variants that have mutations (deletions, insertions or substitutions) within the CDRs of a parent specific binding agent or antibody and selecting variants that have improved biological properties such as binding affinity relative to the parent specific binding agent or antibody. A convenient way for generating such substitutional variants is affinity maturation using phage display. Briefly, several hypervariable region sites (e.g. 6-7 sites) are mutated to generate all possible amino substitutions at each site. The specific binding agent or antibody variants thus generated may be displayed in a monovalent fashion from filamentous phage particles as fusions to the gene III product of M13 packaged within each particle. The phage-displayed variants are then screened for their biological activity (e.g. binding affinity).

Alanine scanning mutagenesis can be performed to identify hypervariable region residues that contribute significantly to antigen binding. Alternatively, or in addition, it may be beneficial to analyze a crystal structure of the antigen-antibody complex to identify contact points between the specific binding agent or antibody and the antigen. Such contact residues and neighboring residues are candidates for substitution according to the techniques elaborated herein. Once such variants are generated, the panel of variants is subjected to screening as described herein and specific binding agents or antibodies with superior properties in one or more relevant assays may be selected for further development.

Techniques utilizing gene shuffling and directed evolution may also be used to prepare and screen specific binding agent or antibody variants for desired activity. For example, Jermutus et al., Proc Natl Acad Sci USA. 2001 Jan. 2; 98(1):75-80 reports that tailored in vitro selection strategies based on ribosome display were combined with in vitro diversification by DNA shuffling to evolve either the off-rate or thermodynamic stability of single-chain Fv antibody fragments (scFvs); Fermer et al., Tumour Biol. 2004 January-April; 25(1-2):7-13 reports that use of phage display in combination with DNA shuffling raised affinity by almost three orders of magnitude.

Altered Glycosylation

Specific binding agent or antibody variants can also be produced that have a modified glycosylation pattern relative to the parent specific binding agent or antibody, for example, deleting one or more carbohydrate moieties found in the specific binding agent or antibody, and/or adding one or more glycosylation sites that are not present in the specific binding agent or antibody.

Glycosylation of polypeptides including antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. The presence of either of these tripeptide sequences in a polypeptide creates a potential glycosylation site. Thus, N-linked glycosylation sites may be added to a specific binding agent or antibody by altering the amino acid sequence such that it contains one or more of these tripeptide sequences. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used. O-linked glycosylation sites may be added to a specific binding agent or antibody by inserting or substituting one or more serine or threonine residues to the sequence of the original specific binding agent or antibody.

Other Modifications

Cysteine residue(s) may be removed or introduced in the Fc region, thereby eliminating or increasing interchain disulfide bond formation in this region. The homodimeric specific binding agent or antibody thus generated may have improved internalization capability and/or increased complement-mediated cell killing and antibody-dependent cellular cytotoxicity (ADCC). See Caron et al., J. Exp Med. 176: 1191-1195 (1992) and Shopes, B. J. Immunol. 148: 2918-2922 (1992). Homodimeric specific binding agents or antibodies may also be prepared using heterobifunctional cross-linkers as described in Wolff et al., Cancer Research 53: 2560-2565

(1993). Alternatively, a specific binding agent or antibody can be engineered which has dual Fc regions and may thereby have enhanced complement lysis and ADCC capabilities. See Stevenson et al., *Anti-Cancer Drug Design* 3: 219-230 (1989).

It has been shown that sequences within the CDR can cause an antibody to bind to MHC Class II and trigger an unwanted helper T-cell response. A conservative substitution can allow the specific binding agent or antibody to retain binding activity yet reduce its ability to trigger an unwanted T-cell response.

It is also contemplated that one or more of the N-terminal 20 amino acids of the heavy or light chain are removed.

Modifications to increase serum half-life also may desirable, for example, by incorporation of or addition of a salvage receptor binding epitope (e.g., by mutation of the appropriate region or by incorporating the epitope into a peptide tag that is then fused to the specific binding agent or antibody at either end or in the middle, e.g., by DNA or peptide synthesis) (see, e.g., WO96/32478) or adding molecules such as PEG or other water soluble polymers, including polysaccharide polymers.

The salvage receptor binding epitope preferably constitutes a region wherein any one or more amino acid residues from one or two loops of a Fc domain are transferred to an analogous position of the specific binding agent or antibody or fragment. Even more preferably, three or more residues from one or two loops of the Fc domain are transferred. Still more preferred, the epitope is taken from the $C_H2$ domain of the Fc region (e.g., of an IgG) and transferred to the $C_H1$, $C_H3$, or $V_H$ region, or more than one such region, of the specific binding agent or antibody. Alternatively, the epitope is taken from the $C_H2$ domain of the Fc region and transferred to the $C_L$ region or $V_L$ region, or both, of the specific binding agent or antibody fragment. See also International applications WO 97/34631 and WO 96/32478 which describe Fc variants and their interaction with the salvage receptor.

The regulation of IgG homeostasis in vivo depends upon its binding to the FcRn. Modification of the interaction between the Fc domain of IgG and FcRn has been reported to improve the serum half-life of monoclonal antibodies. Mutations in the Fc that result in higher affinity binding to neonatal Fc receptor FcRn and slowing degradation and improving PK profile would be preferable. The FcRn binding site on IgG is located at the $C_H2$-$C_H3$ domain interface. Mutations of residues in this area (M428L and T250Q/M428L, T250Q/M428L, P257I/Q311I, M252Y/S254T/T256E, H433K/N434F/Y436H, or M252Y/S254T/T256E/H433K/N434F/Y436H) result in increased affinity of IgG1 for human FcRn at pH 6.0 and pH 7.3. Additionally, some of these mutations resulted in enhanced pharmacokinetic properties (slower clearance, longer half-life) when given intravenously to monkeys.

Other sites of the constant region have been identified that are responsible for complement dependent cytotoxicity (CDC), such as the C1q binding site and/or the antibody-dependent cellular cytotoxicity (ADCC) [see, e.g., Molec. Immunol. 29 (5): 633-9 (1992); Shields et al., J. Biol. Chem., 276(9):6591-6604 (2001), incorporated by reference herein in its entirety]. Mutation of residues within Fc receptor binding sites can result in altered (i.e. increased or decreased) effector function, such as altered ADCC or CDC activity, or altered half-life. As described above, potential mutations include insertion, deletion or substitution of one or more residues, including substitution with alanine, a conservative substitution, a non-conservative substitution, or replacement with a corresponding amino acid residue at the same position from a different subclass (e.g. replacing an IgG1 residue with a corresponding IgG2 residue at that position).

Other Covalent Modifications

Covalent modifications of the specific binding agent or antibody are also included within the scope of this invention. They may be made by chemical synthesis or by enzymatic or chemical cleavage of the specific binding agent or antibody, if applicable. Other types of covalent modifications can be introduced into the specific binding agent or antibody by reacting targeted amino acid residues with an organic derivatizing agent that is capable of reacting with selected side chains or the N- or C-terminal residues.

Cysteinyl residues most commonly are reacted with α-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, .alpha.-bromo-β-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylpyrocarbonate at pH 5.5-7.0 because this agent is relatively specific for the histidyl side chain. Para-bromophenacyl bromide also is useful; the reaction is preferably performed in 0.1 M sodium cacodylate at pH 6.0.

Lysinyl and amino-terminal residues are reacted with succinic or other carboxylic acid anhydrides. Derivatization with these agents has the effect of reversing the charge of the lysinyl residues. Other suitable reagents for derivatizing .alpha.-amino-containing residues include imidoesters such as methyl picolinimidate, pyridoxal phosphate, pyridoxal, chloroborohydride, trinitrobenzenesulfonic acid, O-methylisourea, 2,4-pentanedione, and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high $pK_a$ of the guanidine functional group. Furthermore, these reagents may react with the groups of lysine as well as the arginine epsilon-amino group.

The specific modification of tyrosyl residues may be made, with particular interest in introducing spectral labels into tyrosyl residues by reaction with aromatic diazonium compounds or tetranitromethane. Most commonly, N-acetylimidizole and tetranitromethane are used to form O-acetyl tyrosyl species and 3-nitro derivatives, respectively. Tyrosyl residues are iodinated using $^{125}I$ or $^{131}I$ to prepare labeled proteins for use in radioimmunoassay.

Carboxyl side groups (aspartyl or glutamyl) are selectively modified by reaction with carbodiimides (R—N.dbd.C.dbd.N—R'), where R and R' are different alkyl groups, such as 1-cyclohexyl-3-(2-morpholinyl-4-ethyl) carbodiimide or 1-ethyl-3-(4-azonia-4,4-dimethylpentyl) carbodiimide. Furthermore, aspartyl and glutamyl residues are converted to asparaginyl and glutaminyl residues by reaction with ammonium ions.

Glutaminyl and asparaginyl residues are frequently deamidated to the corresponding glutamyl and aspartyl residues, respectively. These residues are deamidated under neutral or basic conditions. The deamidated form of these residues falls within the scope of this invention.

Other modifications include hydroxylation of proline and lysine, phosphorylation of hydroxyl groups of seryl or threonyl residues, methylation of the .alpha.-amino groups of lysine, arginine, and histidine side chains (T. E. Creighton, Proteins: Structure and Molecular Properties, W.H.

Freeman & Co., San Francisco, pp. 79-86 (1983)), acetylation of the N-terminal amine, and amidation of any C-terminal carboxyl group.

Another type of covalent modification involves chemically or enzymatically coupling glycosides to the specific binding agent or antibody. These procedures are advantageous in that they do not require production of the specific binding agent or antibody in a host cell that has glycosylation capabilities for N- or O-linked glycosylation. Depending on the coupling mode used, the sugar(s) may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of phenylalanine, tyrosine, or tryptophan, or (f) the amide group of glutamine. These methods are described in WO87/05330 published 11 Sep. 1987, and in Aplin and Wriston, CRC Crit. Rev. Biochem., pp. 259-306 (1981).

Removal of any carbohydrate moieties present on the specific binding agent or antibody may be accomplished chemically or enzymatically. Chemical deglycosylation requires exposure of the specific binding agent or antibody to the compound trifluoromethanesulfonic acid, or an equivalent compound. This treatment results in the cleavage of most or all sugars except the linking sugar (N-acetylglucosamine or N-acetylgalactosamine), while leaving the specific binding agent or antibody intact. Chemical deglycosylation is described by Hakimuddin, et al. Arch. Biochem. Biophys. 259: 52 (1987) and by Edge et al. Anal. Biochem., 118: 131 (1981). Enzymatic cleavage of carbohydrate moieties on a specific binding agent or antibody can be achieved by the use of a variety of endo- and exo-glycosidases as described by Thotakura et al. Meth. Enzymol. 138: 350 (1987).

Another type of covalent modification of the specific binding agent or antibody comprises linking the specific binding agent or antibody to one of a variety of nonproteinaceous polymers, e.g., polyethylene glycol, polypropylene glycol, polyoxyethylated polyols, polyoxyethylated sorbitol, polyoxyethylated glucose, polyoxyethylated glycerol, polyoxyalkylenes, or polysaccharide polymers such as dextran. Such methods are known in the art, see, e.g. U.S. Pat. Nos. 4,640, 835; 4,496,689; 4,301,144; 4,670,417; 4,791,192, 4,179,337, 4,766,106, 4,179,337, 4,495,285, 4,609,546 or EP 315 456.

Therapeutic Uses

"Treatment" is an intervention performed with the intention of preventing the development or altering the pathology of a disorder. Accordingly, "treatment" refers to both therapeutic treatment and prophylactic or preventative measures. Those in need of treatment include those already with the disorder as well as those in which the disorder is to be prevented.

"Mammal" for purposes of treatment refers to any animal classified as a mammal, including humans, domestic and farm animals, and zoo, sports, or pet animals, such as dogs, horses, cats, cows, etc. Preferably, the mammal is human.

As used herein, the phrase "therapeutically effective amount" is meant to refer to an amount of therapeutic or prophylactic humanized c-Kit antibody that provides a reduction in mast cell or progenitor cell number and/or activity, reduction in fibroid elements or their precursors, or that provides a reduction in the severity or progression of symptoms associated with c-kit associated disease (i.e. that provides "therapeutic efficacy"). Mast cells and progenitor hematopoietic pluripotent stem cells are the primary cell types expressing c-Kit and thus it is contemplated that cells derived from HSC such as mast cells and that are involved in diseases can be treated with the compositions and methods of the invention.

The phrase "fibrotic-reducing activity" is meant to refer to the ability to inhibit, fully or partially and reverse inflammation resulting from immune system activation and fibrosis.

As used herein the term "fibrotic disease or disorder" refers to conditions involving fibrosis in one or more tissues. As used herein the term "fibrosis" refers to abberant formation or development of excess fibrous connective tissue in an organ or tissue as a reactive process, as opposed to formation of fibrous tissue as a normal constituent or healing of an organ or tissue. Fibrosis is characterized by fibroblast accumulation and collagen deposition in excess of normal deposition in any particular tissue. As used herein the term "fibrosis" is used synonymously with "aberrant healing, involving mesenchymal-fibroblast cell transformation, excessive fibroblast proliferation, activity and deposition of collagens and other extracellular matrix proteins".

Fibroblasts are connective tissue cells, which are dispersed in connective tissue throughout the body. Fibroblasts secrete a nonrigid extracellular matrix containing type I and/or type III collagen. In response to an injury to a tissue, nearby fibroblasts or mesenchymal precursor cells in circulation migrate into the wound, may become alternatively activated under the influence of other cells such as mast cells and their mediators, proliferate, and produce large amounts of collagenous extracellular matrix. Collagen is a fibrous protein rich in glycine and proline that is a major component of the extracellular matrix and connective tissue, cartilage, and bone. Collagen molecules are triple-stranded helical structures called $\alpha$-chains, which are wound around each other in a ropelike helix. Collagen exists in several forms or types; of these, type I, the most common, is found in skin, tendon, and bone; and type III is found in skin, blood vessels, and internal organs.

Mast cell associated fibrotic diseases include pathological fibrosis or scarring (including endocardial sclerosis), idiopathic interstitial fibrosis, interstitial pulmonary fibrosis, perimuscular fibrosis, Symmers' fibrosis, pericentral fibrosis, hepatitis, dermatofibroma, billary cirrhosis, alcoholic cirrhosis, acute pulmonary fibrosis, idiopathic pulmonary fibrosis, acute respiratory distress syndrome, kidney fibrosis/glomerulonephritis, kidney fibrosis/diabetic nephropathy, scleroderma/systemic, scleroderma/local, keloids, hypertrophic scars, severe joint adhesions/arthritis, myelofibrosis, corneal scarring, cystic fibrosis, muscular dystrophy (duchenne's), cardiac fibrosis, muscular fibrosis/retinal separation, esophageal stricture and payronles disease. Further fibrotic disorders may be induced or initiated by surgery, including scar revision/plastic surgeries, glaucoma, cataract fibrosis, corneal scarring, joint adhesions, graft vs. host disease, tendon surgery, nerve entrapment, dupuytren's contracture, OB/GYN adhesions/fibrosis, pelvic adhesions, peridural fibrosis, restenosis. It is also contemplated that fibrotic conditions where deposition of fibronectin is a causative factor can be treated according to the invention. Idiopathic pulmonary fibrosis, bleomycin lung, cystic fibrosis, and glomerular nephropathy, including disease characterized by Fn deposits in the kidneys ultimately leading to renal failure are examples of conditions which can also be treated in accordance with the present invention. Inflammation involving activation of the immune system and where mast cells secrete inflammatory cytokines such as TNF, and can activate and directly interact with lymphocytes can also be treated in accordance with the present invention.

Scleroderma is believed to be an autoimmune disease of the connective tissue resulting in a fibrotic disorder characterized by a thickening and induration of the skin caused by the overproduction of new collagen by fibroblasts in skin and other organs. Scleroderma may occur as a local or systemic disease involving a number of organs. Scleroderma is also referred to as systemic sclerosis. The development of scleroderma pathologies is associated with increased mast cell numbers in the affected disease tissues/organs.

Systemic sclerosis is characterized by formation of hyalinized and thickened collagenous fibrous tissue, with thickening of the skin and adhesion to underlying tissues, especially of the hands and face. The disease may also be characterized by dysphagia due to loss of peristalsis and submucosal fibrosis of the esophagus, dyspnea due to pulmonary fibrosis, myocardial fibrosis, and renal vascular changes. (Stedman's Medical Dictionary, 26$^{th}$ Edition, Williams & Wilkins, 1995)). Pulmonary fibrosis affects 30 to 70% of scleroderma patients, often resulting in restrictive lung disease (Atamas et al. *Cytokine and Growth Factor Rev* 14: 537-550 (2003)). Some patients have an overlap of scleroderma and other connective tissue diseases, such as rheumatoid arthritis, systemic lupus erythematosus, and polymyositis. When features of scleroderma are present along with features of polymyositis and systemic lupus erythematosus, the condition is referred to as mixed connective tissue disease (MCTD).

It is known that the symptoms present in some forms of dermatitis are caused by degranulation of cutaneous mast cells, resulting in, inter alia, histamine release. Thus, another mast cell associated disorder suitable for treatment according to the invention is urticaria pigmentosa. This disorder presents characteristic skin lesions that are single or multiple pigmented macules or nodules that urticate on rubbing and contain large numbers of mast cells. There are different forms of associated dermatitis (inflammation of skin) such as erythema, edema, papular eruptions and pruritus may be present in both human and animal dermatitides, all of which are treatable according to the invention.

Mastocytosis is in many cases a neoplastic disease and involves new or abnormal mast cell growth and may be a consequence of elevated SCF autocrine signaling or an activating c-Kit mutation. Mastocytosis may be limited or systemic involving multiple organs such as the bone marrow. Mast cells release certain mediators, or chemicals, of which one is histamine, into the body in response to certain events. People with systemic mastocytosis develop an increase in the number of mast cells, or they develop abnormally shaped mast cells, which may not function properly. In addition, the mast cells fail to die off when they are supposed to, further increasing the total mast cell burden. When the mast cells degranulate and release their contents it can cause many acute and potentially serious conditions or diseases. Mast cell disorders also include proliferative disorders resulting in localized disease such as solitary cutaneous mastocytoma up to the more severe disease of mast cell leukemia. Examples include cutaneous mastocytoma, aggressive mastocytosis, indolent mastocytosis, mastocytosis with associated hematologic disorder, urticaria pigmentosa, telangiectasia macularis eruptiva perstans (tmep), systemic mast cell disease, mast cell leukemia, myeloid leukemia, systemic mastocytosis (with or without cutaneous manifestations such as urticaria pigmentosa), mast cell activation syndrome/disorder, and more common pediatric mast cell disorders such as solitary mastocytoma and diffuse cutaneous mastocytosis.

Mast cell activation syndrome or disorder is characterized by a normal or nearly normal number of mast cells. However, the mast cells are easily triggered to release their contents, which results in many of the same symptoms. The danger of anaphylaxis and shock is present with this disorder, but unlike proliferative disorders of mast cells, this syndrome may not have the potential to progress to a more aggressive or malignant stage. Examples of such disorders associated with mast cell degranulation can include abdominal pain, hives and rashes, anaphylaxis, inflammation of the esophagus, blood pressure changes and shock, intestinal cramping and bloating, bone pain (mild to severe/debilitating), itching, with and without rashes, chest pain, liver, spleen and other organ involvement, cognitive difficulties/brain fog, malabsorption, degenerative disc disease, migraine headaches, diarrhea, muscle pain, dizziness/vertigo/lightheadedness, nausea, faintness, osteoporosis/osteopenia, fatigue, peripheral neuropathy and paresthesias, flushing, rapid heart rate, gastroesophageal reflux, and vomiting.

The role of mast cells in allergic diseases has been clinically validated by drugs that block mast cell specific mediators such as histamine and corticosteroids which among their activities cause mast cell apoptosis. Additional mast cell related diseases include histamine-mediated allergic reactions that can be treated by inhibiting chemokine-induced mast cell and basophil degranulation and release of histamine. Examples of mast cell associated disorders or diseases which may be effectively treated with the subject methods and compositions also include, but are not limited to, contact dermatitis, atopic dermatitis, allergic dermatitis, eczematous dermatitis and dermatitis caused by insect bites or stings.

Other mast cell related indications suitable for treatment by the methods and compositions of the invention include pulmonary inflammatory conditions in interstitial lung diseases for example sarcoidosis, neonatal respiratory distress syndrome (RDS), bronchopulmonary dysplasia (BPD), and conditions characterized by an elevation in serum PLA2 activity, such as adult RDS (ARDS).

Mast cells have also been published to show roles in arthritis. Mast cells are increased in the inflamed synovial tissues of RA and OA patients, and Gleevec has been shown to cause mast cell apoptosis in synovial explants and human case studies show efficacy in RA patients. Mast cells have roles in septic shock, pancreatitis, collagen vascular diseases, acute renal failure, peritonitis, and autoimmune uveitis.

Studies also suggest that mast cells participate in the pathophysiology of multiple sclerosis. It is thought that mast cells in the brain release vasoactive amines which may cause demyelination. Histamine released from mast cells may alter blood vessel integrity and cause partial breakdown of the blood-brain barrier again implicated in the etiology of multiple sclerosis. Thus, it is contemplated that the methods and compositions of the invention are suitable for treatment or amelioration of the morbidity associated with multiple sclerosis.

C-kit is also expressed on certain non-immune cells such as melanocytes and intestinal cells as well as spermatocytes. The invention may have utility in the treatment of melanoma and GIST and may have utility as a male contraceptive.

Administration and Preparation of Pharmaceutical Formulations

The anti-c-Kit specific binding agents or antibodies used in the practice of a method of the invention may be formulated into pharmaceutical compositions comprising a carrier suitable for the desired delivery method. Suitable carriers include any material which, when combined with the anti-c-Kit specific binding and neutral antagonist agent or antibody, retains the high-affinity binding and potency at c-Kit and is nonreactive with the subject's immune systems. Examples include, but are not limited to, any of a number of standard pharmaceutical carriers such as sterile phosphate buffered saline solutions, bacteriostatic water, and the like. A variety of aqueous carriers may be used, e.g., water, buffered water, 0.4% saline, 0.3% glycine and the like, and may include other proteins for enhanced stability, such as albumin, lipoprotein, globulin, etc., subjected to mild chemical modifications or the like.

Exemplary antibody concentrations in the formulation may range from about 0.1 mg/ml to about 180 mg/ml or from about 0.1 mg/mL to about 50 mg/mL, or from about 0.5 mg/mL to about 25 mg/mL, or alternatively from about 2 mg/mL to about 10 mg/mL. An aqueous formulation of the antibody may be prepared in a pH-buffered solution, for example, at pH ranging from about 4.5 to about 6.5, or from about 4.8 to about 5.5, or alternatively about 5.0. Examples of buffers that are suitable for a pH within this range include acetate (e.g. sodium acetate), succinate (such as sodium succinate), gluconate, histidine, citrate and other organic acid buffers. The buffer concentration can be from about 1 mM to about 200 mM, or from about 10 mM to about 60 mM, depending, for example, on the buffer and the desired isotonicity of the formulation.

A tonicity agent, which may also stabilize the antibody, may be included in the formulation. Exemplary tonicity agents include polyols, such as mannitol, sucrose or trehalose. Preferably the aqueous formulation is isotonic, although hypertonic or hypotonic solutions may be suitable. Exemplary concentrations of the polyol in the formulation may range from about 1% to about 15% w/v.

A surfactant may also be added to the antibody formulation to reduce aggregation of the formulated antibody and/or minimize the formation of particulates in the formulation and/or reduce adsorption. Exemplary surfactants include nonionic surfactants such as polysorbates (e.g. polysorbate 20, or polysorbate 80) or poloxamers (e.g. poloxamer 188). Exemplary concentrations of surfactant may range from about 0.001% to about 0.5%, or from about 0.005% to about 0.2%, or alternatively from about 0.004% to about 0.01% w/v.

In one embodiment, the formulation contains the above-identified agents (i.e. antibody, buffer, polyol and surfactant) and is essentially free of one or more preservatives, such as benzyl alcohol, phenol, m-cresol, chlorobutanol and benzethonium C1. In another embodiment, a preservative may be included in the formulation, e.g., at concentrations ranging from about 0.1% to about 2%, or alternatively from about 0.5% to about 1%. One or more other pharmaceutically acceptable carriers, excipients or stabilizers such as those described in Remington's Pharmaceutical Sciences 16th edition, Osol, A. Ed. (1980) may be included in the formulation provided that they do not adversely affect the desired characteristics of the formulation. Acceptable carriers, excipients or stabilizers are nontoxic to recipients at the dosages and concentrations employed and include; additional buffering agents; co-solvents; antoxidants including ascorbic acid and methionine; chelating agents such as EDTA; metal complexes (e.g. Zn-protein complexes); biodegradable polymers such as polyesters; and/or salt-forming counterions such as sodium.

Therapeutic formulations of the antibody are prepared for storage by mixing the antibody having the desired degree of purity with optional physiologically acceptable carriers, excipients or stabilizers (Remington's Pharmaceutical Sciences 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, maltose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

In one embodiment, a suitable formulation of the claimed invention contains an isotonic buffer such as a phosphate, acetate, or TRIS buffer in combination with a tonicity agent such as a polyol, Sorbitol, sucrose or sodium chloride which tonicifies and stabilizes. One example of such a tonicity agent is 5% Sorbitol or sucrose. In addition, the formulation could optionally include a surfactant such as to prevent aggregation and for stabilization at 0.01 to 0.02% wt/vol. The pH of the formulation may range from 4.5-6.5 or 4.5 to 5.5. Other exemplary descriptions of pharmaceutical formulations for antibodies may be found in US 2003/0113316 and U.S. Pat. No. 6,171,586, each incorporated herein by reference in its entirety.

The formulation herein may also contain more than one active compound as necessary for the particular indication being treated, preferably those with complementary activities that do not adversely affect each other. For example, it may be desirable to further provide an immunosuppressive agent. Such molecules are suitably present in combination in amounts that are effective for the purpose intended.

The active ingredients may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

Suspensions and crystal forms of antibodies are also contemplated. Methods to make suspensions and crystal forms are known to one of skill in the art.

The formulations to be used for in vivo administration must be sterile. The compositions of the invention may be sterilized by conventional, well known sterilization techniques. For example, sterilization is readily accomplished by filtration through sterile filtration membranes. The resulting solutions may be packaged for use or filtered under aseptic conditions and lyophilized, the lyophilized preparation being combined with a sterile solution prior to administration.

The process of freeze-drying is often employed to stabilize polypeptides for long-term storage, particularly when the polypeptide is relatively unstable in liquid compositions. A lyophilization cycle is usually composed of three steps: freezing, primary drying, and secondary drying; Williams and Polli, Journal of Parenteral Science and Technology, Volume 38, Number 2, pages 48-59 (1984). In the freezing step, the solution is cooled until it is adequately frozen. Bulk water in the solution forms ice at this stage. The ice sublimes in the primary drying stage, which is conducted by reducing chamber pressure below the vapor pressure of the ice, using a vacuum. Finally, sorbed or bound water is removed at the secondary drying stage under reduced chamber pressure and an elevated shelf temperature. The process produces a material known as a lyophilized cake. Thereafter the cake can be reconstituted prior to use.

The standard reconstitution practice for lyophilized material is to add back a volume of pure water (typically equivalent to the volume removed during lyophilization), although dilute solutions of antibacterial agents are sometimes used in the production of pharmaceuticals for parenteral administration; Chen, Drug Development and Industrial Pharmacy, Volume 18, Numbers 11 and 12, pages 1311-1354 (1992).

Excipients have been noted in some cases to act as stabilizers for freeze-dried products; Carpenter et al., Developments in Biological Standardization, Volume 74, pages 225-239 (1991). For example, known excipients include polyols (including mannitol, sorbitol and glycerol); sugars (including glucose and sucrose); and amino acids (including alanine, glycine and glutamic acid).

In addition, polyols and sugars are also often used to protect polypeptides from freezing and drying-induced damage and to enhance the stability during storage in the dried state. In general, sugars, in particular disaccharides, are effective in both the freeze-drying process and during storage. Other classes of molecules, including mono- and di-saccharides and polymers such as PVP, have also been reported as stabilizers of lyophilized products.

For injection, the pharmaceutical formulation and/or medicament may be a powder suitable for reconstitution with an appropriate solution as described above. Examples of these include, but are not limited to, freeze dried, rotary dried or spray dried powders, amorphous powders, granules, precipitates, or particulates. For injection, the formulations may optionally contain stabilizers, pH modifiers, surfactants, bioavailability modifiers and combinations of these.

Sustained-release preparations may be prepared. Suitable examples of sustained-release preparations include semipermeable matrices of solid hydrophobic polymers containing the antibody, which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and y ethyl-L-glutamate, non-degradable ethylene-vinyl acetate, degradable lactic acid-glycolic acid copolymers such as the Lupron Depot™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

The formulations of the invention may be designed to be short-acting, fast-releasing, long-acting, or sustained-releasing as described herein. Thus, the pharmaceutical formulations may also be formulated for controlled release or for slow release.

Specific dosages may be adjusted depending on conditions of disease, the age, body weight, general health conditions, sex, and diet of the subject, dose intervals, administration routes, excretion rate, and combinations of drugs. Any of the above dosage forms containing effective amounts are well within the bounds of routine experimentation and therefore, well within the scope of the instant invention.

The specific binding agent or antibody is administered by any suitable means, including parenteral, subcutaneous, intraperitoneal, intrapulmonary, and intranasal, and, if desired for local treatment, intralesional administration. Parenteral infusions include intravenous, intraarterial, intraperitoneal, intramuscular, intradermal or subcutaneous administration. In addition, the specific binding agent or antibody is suitably administered by pulse infusion, particularly with declining doses of the specific binding agent or antibody. Preferably the dosing is given by injections, most preferably intravenous or subcutaneous injections, depending in part on whether the administration is brief or chronic. Other administration methods are contemplated, including topical, particularly transdermal, transmucosal, rectal, oral or local administration e.g. through a catheter placed close to the desired site. Most preferably, the specific binding agent or antibody of the invention is administered intravenously in a physiological solution at a dose ranging between 0.01 mg/kg to 100 mg/kg at a frequency ranging from daily to weekly to monthly (e.g. every day, every other day, every third day, or 2, 3, 4, 5, or 6 times per week), preferably a dose ranging from 0.1 to 45 mg/kg, 0.1 to 15 mg/kg or 0.1 to 10 mg/kg at a frequency of 2 or 3 times per week, or up to 45 mg/kg once a month.

Administration with Other Agents

The antibodies of the invention also may be concurrently administered with other anti-inflammatory therapeutic agents. Concurrent administration includes administration of the two different therapeutic agents at different times and at different routes, as long as there is some overlap in the time during which the agents are exerting their therapeutic effects. Exemplary anti-c-Kit agents known in the art include Imatinib Mesylate (Gleevec™). It should be noted that Imatinib Mesylate also antagonizes signaling from the Abl tyrosine kinase and therefore is not a specific c-Kit inhibitor.

EXAMPLES

Humanization of SR-1

SR-1 was humanized by a straight CDR graft, with surprisingly no back mutations required to maintain affinity though it remained to be demonstrated desired functional activity. The human frameworks that maintained the most canonical residues, and did not introduce additional proline residues, were chosen as acceptor sequences. Based on these criteria, the heavy chain acceptor sequence was VH1 1-46 for framework I and II and VH1 1-e for framework III, with JH4 as the closest J region (also known as framework IV). The light chain acceptor sequence was the VK4 B3 germline sequence with JK2 as the closest J region.

Isotype switching was done to produce human IgG2, IgG1, IgG4P and aglycosylated IgG1 forms of the humanized antibody. The N-linked glycosylation consensus site was removed from the human IgG1 constant region sequence by mutation of a single residue from asparagine to glutamic acid at position 297 (Kabat numbering).

The humanized SR-1 in the aglycosylated IgG1 (hSR-1 aIgG1) form binds in a desired manner with higher affinity to the membrane c-Kit compared to soluble c-kit, and is a highly potent neutral antagonist of SCF and mediating no agonism of c-Kit directly in all cell based assays tested using proximal and distal read-outs of c-Kit signaling. The aglycosylated IgG1 isotype was chosen to avoid effector function and cell killing through bystander effects. This antibody showed an unexpected and desired half-life, nonlinear PK and saturable target-mediated antibody elimination in monkeys. It also depletes mast cells in vivo as expected.

Binding to c-Kit Dimer

Activation of c-Kit upon binding by stem cell factor (SCF) leads to dimerization/oligomerization, autophosphorylation and receptor internalization, most likely through a clathrin-dependent pathway. The SR-1 monoclonal antibody binds the c-Kit dimer with 1000-fold higher affinity compared to the soluble c-Kit extra-cellular domain monomer as determined by Biacore. Kinetic modeling suggests that SR-1 would preferentially bind the native membrane-associated receptor even in the presence of ng/mL of the soluble shed receptor monomer.

Carbohydrates present on a glycoprotein can influence biological and functional properties. Humanization of SR-1 to an aglycosylated IgG1 form showed that binding parameters were conserved. Humanized SR-1 aIgG1 bound to recombinant c-Kit receptor-Fc with a KinExA Equilibrium Binding Kd of 1.0 pM and using the Biacore assay, hSR-1 aIgG1 blocked stem cell factor (SCF) binding with a Ki=70 pM. hSR-1 aIgG1 binds with high affinity to the receptor dimer versus monomer. This is an important characteristic not predicted to be translated with certainty with the humanization and as the soluble c-Kit monomer is less likely to act as a sink for the antibody in vivo.

Inhibition of c-Kit Dependent Cell Survival and Receptor Signaling

The human megakaryoblastic cell line UT-7 is dependent on SCF for survival and the removal of SCF or its inhibition results in rapid loss of viability and decreased proliferation. This assay is suited for IC50 potency determination of SCF antagonists. hSR-1 aIgG1 exhibited a mean IC50 of 35 pM.

hSR-1 aIgG1 potently inhibited SCF-mediated c-Kit phosphorylation and internalization in MO7e cells indicating that the antibody can block SCF-mediated c-Kit signaling events. In contrast to findings of SR-1 being capable of intrinsically mediating c-Kit internalization and phosphorylation, surprisingly, no evidence of agonism was detected in the MO7e c-Kit receptor proximal phosphorylation read-out for hSR-1 aIgG1. Notably, hSR-1 IgG2, the IgG2 antibody was slightly less potent and did not fully inhibit SCF-mediated c-Kit receptor internalization.

hSR-1 aIgG1 shows neutralization at 1.0 ug/mL of the synergistic effect of SCF on GM-CSF derived colony formation using primary isolated human CD34+, CD 117+ (c-Kit) bone marrow cells. Consistent with our novel finding that hSR-1 aIgG1 did not mediate c-Kit internalization or phosphorylation, and no intrinsic agonistic survival activity of hSR-1 aIgG1 was observed up to 10 ug/mL concentration of the antibody in this assay. In fact, the antibody was able to inhibit survival below baseline.

Lack of Mast Cell Aggregation, CDC and FcR Activity

Figure 3:
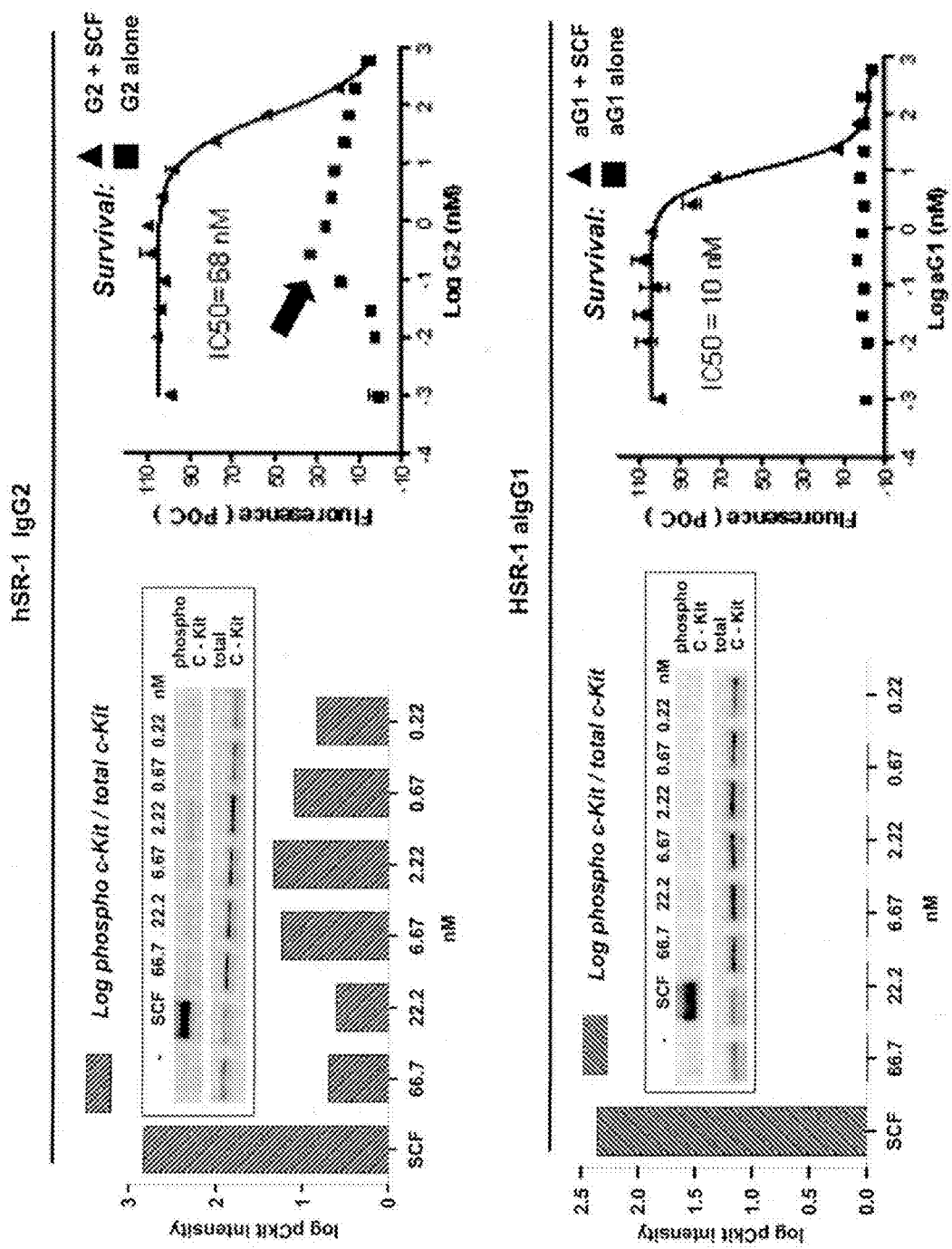
FIG. 3: Humanized SR-1 isoforms inhibit stem cell factor (SCF) induced activation of c-Kit and subsequent phosphorylation via c-Kit.

Cultured human mast cells derived from bone marrow CD34+ cells were used to assess the apparent potency and rank order of compounds. hSR-1 aIgG1 inhibited SCF-dependent mast cell survival, conferred no survival signal to mast cells, did not mediate c-Kit receptor phosphorylation (FIG. 3) and showed no ability to mediate homotypic mast cell aggregation. In contrast, the hSR-1 IgG2 was able to block SCF-mast cell survival but itself showed partial agonist activity conferring a survival signal, mediating c-Kit receptor phosphorylation and resulted in a reproducible effect on mast cell clustering. No unexpected abnormalities were observed for hSR-1 aIGg1 when this antibody was dosed in vivo up to 30 mg/kg once weekly for 4 weeks or up to 150 mg/kg subcutaneously once weekly for 2 weeks in non-human primates.

hSR-1 aIgG1 shows no detectable non-specific FcR binding to U-937 cells expressing Fcγ receptor I=CD64, Fcγ receptor II=CD32 and Fcγ receptor III=CD16. In contrast, binding of SR-1 IgG1 and IgG4β isotypes was detected presumably to the high affinity FcγRI. Therefore no ADCC activity is predicted for hSR-1 aIgG1, and experimental data to date show no complement dependent cytotoxic cell death. Aglycosylated chimeric mouse/human IgG1 antibodies have been reported to retain some effector function (Hybridoma. 1991 April; 10(2):211-7) and so these desired activities of hSR-1 aIgG1 are not expected. The data shows that application of standard methodologies and therefore choice of typical IgG2 or IgG1 or IgG4 isotypes would have not yielded a molecule with appropriate characteristics, that is a high-affinity binder, functional neutral antagonist at c-kit and that would not activate mast cells.

Pharmacokinetics

A preliminary PK study was conducted to compare hSR-1 IgG2 and hSR-1 aIgG1 PK in male cynomolgus monkeys after a single IV or SC administration at 3 mg/kg. Time profiles indicate a non-linear PK for both. The concentrations decreased more rapidly at lower concentrations. The two antibodies showed similar exposures, as measured by $C_0/C_{max}$ and $AUC_{0-tlast}$, after a single IV or SC administration in cynomolgus monkeys. Based on $AUC_{0-tlast}$, the serum clearance was approximately ≤0.3 mL/hr/kg for both humanized antibodies. The bioavailability was approximately 82% and 69% for the hSR-1 aIgG1 and hSR-1 IgG2 humanized SR-1 versions, respectively, after SC dosing.

Based on preliminary exposure data of SR-1 and humanized antibodies in African green monkeys after repeated once-weekly dosing, humanized antibodies achieved higher exposures compared to SR-1. Notably, hSR-aIgG1 showed equal best in group PK and it has been demonstrated previously that the degree of glycosylation of a molecule may alter its pharmacokinetic properties and, in the case of an antibody, its metabolism and other biological properties Cancer Immunol Immunother. 1992; 35(3): 165-74.

TABLE 1

Pharmacokinetic Parameter Estimates After a Single IV or SC Administration of hSR-1 IgG2 or hSR-1 aIgG1 at 3 mg/kg to Male Cynomolgus Monkeys

| Test article | Dose route | $C_0/C_{max}$ (μg/mL) | $T_{max}$ (hr) | $AUC_{0-tlast}$ (hr * μg/mL) | CL or CL/F[a] (mL/hr/kg) | F % |
|---|---|---|---|---|---|---|
| hSR-1 aIgG1 | IV | 103 | — | 9710 | ≤0.309 | — |
| hSR-1 IgG2 | IV | 107 | — | 10600 | ≤0.283 | — |

TABLE 1-continued

Pharmacokinetic Parameter Estimates After a Single IV or SC Administration of hSR-1 IgG2 or hSR-1 aIgG1 at 3 mg/kg to Male Cynomolgus Monkeys

| Test article | Dose route | $C_0/C_{max}$ (µg/mL) | $T_{max}$ (hr) | $AUC_{0-tlast}$ (hr * µg/mL) | CL or CL/F$^a$ (mL/hr/kg) | F % |
|---|---|---|---|---|---|---|
| hSR-1 aIgG1 | SC | 36.4 | 72 | 7970 | ≤0.376 | 82.1 |
| hSR-1 IgG2 | SC | 36.7 | 60 | 7290 | ≤0.412 | 68.8 |

$C_0$ = estimated initial concentration after IV dosing
$C_{max}$ = maximum concentration after SC dosing
$T_{max}$ = time of $C_{max}$
$AUC_{0-tlast}$ = area under the concentration-time curve from time 0 to the last time point with a quantifiable concentration
CL = clearance after IV dosing; CL/F = apparent clearance after SC dosing
F % = bioavailability %
$^a$Clearance calculated based on $AUC_{0-tlast}$
— not applicable
$C_0$, $C_{max}$, $AUC_{0-\{tlast\}}$, CL, CL/F, and F % reported to 3 significant FIGS.

Human Dose Projections

The minimal effective dose in the wound PD model of mast cell expansion is <0.3 mg/Kg administered once weekly for 2 weeks in monkeys. Based on a body surface area-based dose conversion, the minimal effective dose in human is projected to be <0.1 mg/Kg with an equivalent dosing regiment. However, this is a preliminary estimation as the PK and the pharmacodynamic relationship between the degree and duration of c-kit inhibition in human by hSR-1 aIgG1 and clinical endpoints are unknown at this time. A more accurate projection will be made when more pharmacokinetic and pharmacodynamic data are available.

In Vivo Potency: Depletion of Basal Lung and Colon Mast Cells in Monkey with SR-1 and hSR-1 aIGg1

In human, mast cell MCt expressing tryptase and lacking chymase are localized primarily to mucosal tissues such as the lung and colon, and this subtype has been detected in the skin and at higher levels of some scleroderma patients suggesting possible alternative activation of mast cells in this condition. The mast cell MCtc expressing both tryptase and chymase are also colocalized in some of these tissues and similarly have been associated with scleroderma and other fibrotic conditions. Hence both subtypes would represent the primary targets for a c-Kit inhibitor in diseases involving mucosal and connective tissues (eg. IPF, SSc, asthma, RA and IBD). The therapeutic would also need to be highly potent, efficacious and have a good volume of distribution and PK since mast cells are generally long-lived and are tissue-resident. Moreover mast cells are largely quiescent until activated to degranulate and de novo synthesize mediators where they then play a key role in the inflammatory response.

The aims for the in vivo studies were to demonstrate depletion of basal mucosal and connective tissue mast cells such as present in the lung and colon and to determine effects on hematopoiesis and effects on precursor cells as well as an impact on erythropoiesis, melanogenesis and spermatogenesis (therefore utility in male contraception) following sustained and high fractional inhibition of c-Kit. The SR-1 monoclonal antibody was selected based on its equivalent functional potency at human and monkey c-Kit in the CD34+ bone marrow cell CFU assay (inhibition at 1.0 ug/mL), and its monkey PK.

SR-1 was administered at doses ranging from 3 mg/Kg to 30 mg/Kg once weekly for 4 weeks. In time course studies, basal colon mast cells were shown to be maximally depleted after 2 doses by day 14 ($C_{trough}$>800-fold the cell IC50), and thus day 14 was chosen as the time point to determine the pharmacological activity of c-Kit antagonists on basal colon mast cells. For practical reasons, basal pulmonary mast cells were evaluated on day 28 at the time of necropsy and the termination of the study.

At a 3.0 mg/Kg dose of SR-1 administered once weekly, depletion of basal lung mast cells was observed at a $C_{trough}$ PK level of >200-fold the UT-7 cellular IC50. The effects of lower doses of SR-1 on basal colon and lung mast cells, melanogenesis and spermatogenesis were not evaluated.

However, a lower dose study with hSR-1 aIgG1 was performed at 0.3, 1.0 and 3.0 mg/Kg. The day 14 $C_{trough}$ levels were >200, >2000, and >8000-fold the cell IC50 and these $C_{trough}$ levels corresponded to no efficacy, near half-depletion (69%), and near-full depletion (96%) of basal colon mast cells (summarized in Table 1). The exposure, cell potency and effect relationship for hSR-1 aIgG1 is in correspondence with SR-1 findings reported.

In Vivo Efficacy of SR-1 and hSR-1 aIGg1 in the Wound Pharmacodynamic Model of Mast Cell Expansion in Monkey Damage to the skin is followed by a robust inflammatory response, in which first neutrophils and then macrophages and mast cells emigrate from nearby tissues and from the circulation, granulation and, re-epithelialization of tissues, and fibroblast associated contraction of underlying wound connective tissues (Diegelmann R F, et al., Front. Biosci. 2004, January 1; 9:283-9). Cutaneous wound injury is a model to study mechanisms that may be relevant in fibrosis since many of the cell types involved are associated with this disease. Moreover, it has been reported in humans to be coupled with a rise in fibroblast derived SCF and activation and increased densities of mast cells (Trautmann A, et al, J. Pathol. 2000, January; 190(1):100-6). Following cutaneous wound injury in monkey, mast cell numbers increase in a time-dependent manner with a plateau that is reached 14-days post-wounding, which is comparable to the human paradigm.

Doses of 0.3, 1 or 3 mg/Kg of SR-1 administered once weekly led to near maximal inhibition of wound activated expansion of mast cells on day 14 (FIG. 1). Maximal inhibition is defined as the ability to block 100% the increase in mast cells over baseline numbers by day 14 after wounding. $C_{trough}$ levels for the 0.3 mpk dose was >7-fold the UT-7 IC50 on Day 14 (Table 2). By 3 weeks, serum levels were about 2-fold the UT-7 IC50, and at this exposure only partial inhibition was observed (FIG. 1). At 3 weeks, maximal efficacy was still observed for both the 1 and 3 mg/Kg cohorts where serum $C_{trough}$ levels were sustained at >200-fold the IC50. These studies suggest that a sustained $C_{trough}$ exposure of >7-fold the IC50 concentration is likely required for maximal inhibition of wound-expanded mast cells.

Doses of 0.3, 1.0 and 3.0 mg/Kg of hSR-1 aIgG1 were evaluated based on the maximal efficacy shown for SR-1 in this model. At the lowest dose tested (0.3 mg/Kg), maximal inhibition of wound-induced expansion of mast cells was observed within 2 weeks. Serum $C_{trough}$ levels at this time was >200-fold the UT-7 IC50 (Table 2).

Table 2 summarizes the PD/PK effects of SR-1 and hSR-1 aIGg1 in the wound PD model.

| drug | UT-7 IC50 (ng/ml) | Dose | $C_{trough}$ (ng/ml) | Fold UT-7 IC50 | Inhibition of activated skin mast cells | Depletion of basal colon mast cells |
|---|---|---|---|---|---|---|
| SR-1 | 3.6 | 0.3 mg/kg | 30 | 8 | >95% | ND |
| | | 1.0 mg/kg | 994 | 276 | >80% | ND |
| | | 3.0 mg/kg | 1873 | 520 | >80% | ND |

-continued

| drug | UT-7 IC50 (ng/ml) | Dose | $C_{trough}$ (ng/ml) | Fold UT-7 IC50 | Inhibition of activated skin mast cells | Depletion of basal colon mast cells |
|---|---|---|---|---|---|---|
| hSR-1 aIgG1 | 4.5 | 0.3 mg/kg | 910 | >200 | >95% | No effect |
|  |  | 1.0 mg/kg | 12,400 | >2000 | >95% | >65% |
|  |  | 3.0 mg/kg | 44,500 | >7000 | >95% | >95% |

Figure 2:
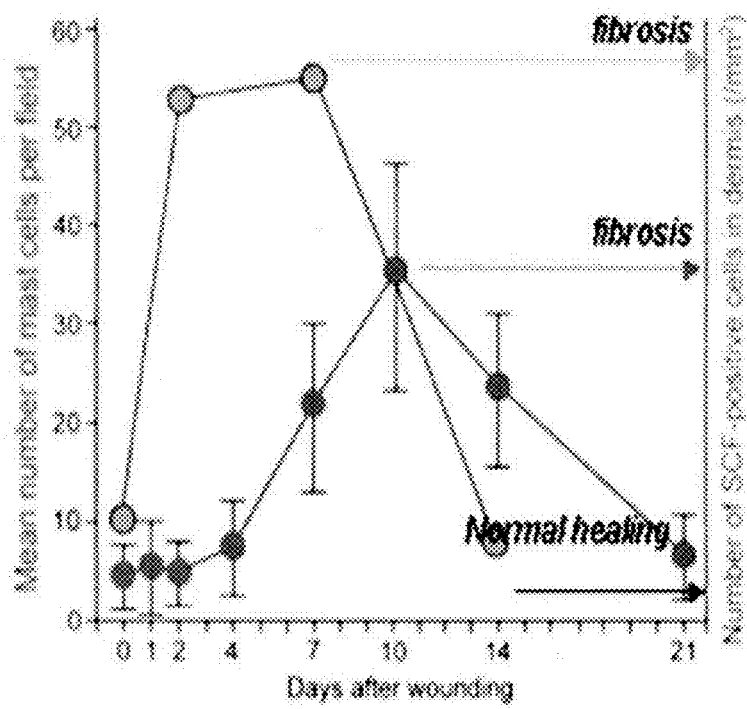
FIG. 2: Mast cell counts in a wound healing model.
Figure 2:
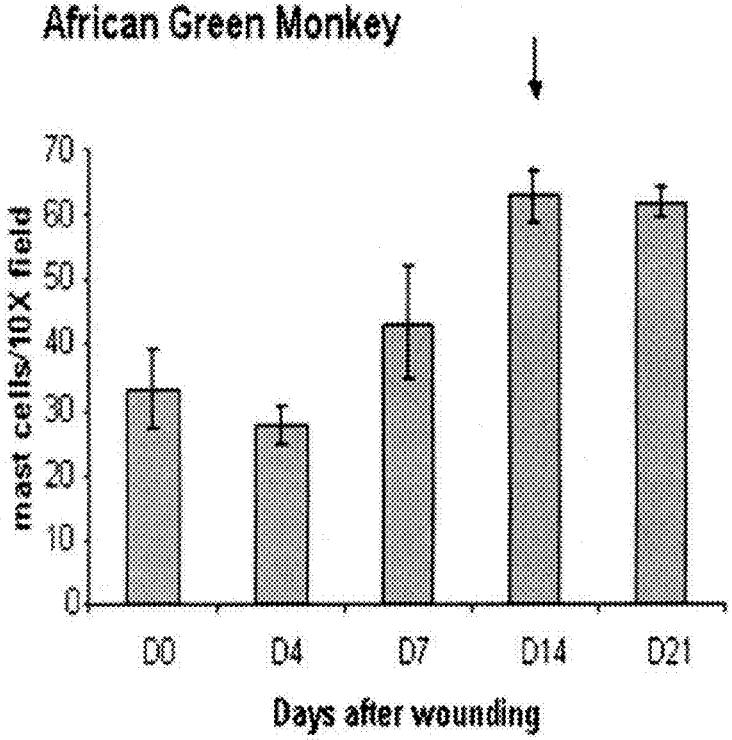

An incisional wound was made followed by punch biopsy up to day 21 in human (left) or non-human primate (right) (FIG. 2). Mast cells and/or SCF expressing fibroblasts were revealed by chromogenic stain or IHC respectively. In human, the expression of SCF rises and returns to baseline and is temporally followed by a transient rise in mast cell numbers during normal wound healing. Similar mast cell response to wounding is observed in monkey. During fibrosis and aberrant wound healing, SCF expression and mast cells numbers remain elevated (FIG. 2).

Hematopoiesis and Melanogenesis

Mouse genetics show that c-Kit plays a role in hematopoiesis during embryonic development, but in human heterozygous inactivating and/or loss-of-function c-Kit mutations in Piebald subjects have not been linked to hematological abnormalities. SCF and c-Kit are important in human hematopoiesis since SCF is used in combination with G-CSF for hematopoietic stem cell mobilization. Moreover, the multi-kinase inhibitor Gleevec which target primarily BCR-ABL, PDGFR and c-Kit has as its primary pharmacological effect myelosuppression, and severe grade 3-4 anemias and thrombocytopenias have been reported in GIST patients (Hensley M L, et al., Semin. Hematol. 2003, April; 40(2 Suppl 2):21-5).

Mouse genetics indicate that c-Kit plays a role in the migration of melanoblasts from the neural crest during embroyogenesis, and this role is supported in human Piebaldism. Gleevec has been reported to cause "banding" depigmentation in the hair in a minor number of GIST patients but this has not been a consistent finding and hyperpigmentation has also been reported. The contribution of other kinases such as PDGF can not be excluded. Studies in mice with multi-kinase inhibitors and a c-Kit antibody show that inhibition of hair pigmentation is fully reversible suggesting that c-Kit inhibition affects melanocyte function and not survival in the postnatal setting (Moss et al, 2003).

SR-1 was used in dose-ranging studies from 3 to 30 mg/Kg administered once weekly for 4 weeks to determine the exposures required to inhibit hematopoiesis, spermatogenesis and active melanogenesis. A full blood panel including cell differentials was performed on blood samples taken at baseline, day 4, 7, 14, 21 and 28 after the start of the study. Analysis of freshly isolated blood samples was performed at the Queen Elizabeth Hospital Clinical Hematology lab, Barbados.

No significant impact of SR-1 compared to control subjects and baseline values was detected on any hematological parameters analyzed though there were non-significant decreases in RBCs in drug treated animals 4 weeks after dosing started. At the highest dose tested, 30 mg/Kg once weekly over 4 weeks, exposure levels of >70,000-fold the UT-7 IC50 potency was achieved. Lack of significant effect on hematological parameters were confirmed by bone marrow histopathological analysis showing no difference between drug treated and control cohorts and no depletion of CD117 positive hematopoietic stem cells suggesting potential redundant pathways for hematopoiesis in the African green monkey NHP species. The effect of 3-30 mpk administered once weekly for 4 weeks on melanogenesis was also examined since there may be utility in melanoma. To assess the effects on activated melanocytes which may better reflect a disease state, hair was depilated to activate melanogenesis. The normal hair color of the coat was not visibly affected in any cohort. However, inhibition of hair pigmentation to variable degrees was observed in newly regrown hair in monkeys receiving the 30 mg/Kg dose. No effect was observed in the 10 mg/Kg cohort suggesting that the no effect dose is between 10-30 mg/Kg. In the 10 mg/Kg cohort, SR-1 exposures were >8000-fold the UT-7 IC50. Maximal efficacy for mast cell depletion was achieved at >7-fold the UT-7 IC50. These data suggests that c-Kit inhibition affects melanocyte function, and that higher doses/exposures may be needed to block in diseases characterized by excessive melanocyte activity.

Spermatogenesis

Mouse studies have shown that c-Kit is important for the maintenance and proliferation of differentiated c-kit receptor-positive spermatogonia but not for the initial step of spermatogonial cell differentiation. Both male and female Piebald subjects that are heterozygote for an inactive c-Kit receptor allele, are fertile suggesting that this degree of c-Kit inactivation, does not appear to affect primordial germ cell development, spermatogenesis or oogenesis.

SR-1 showed dose-dependent inhibition of spermatogenesis from 0.3-30 mg/Kg. The 0.3 mg/Kg once weekly dose is less than the maximal effect observed at the higher doses, and lower dose ranging studies are required to define the ED50. The exposures achieved are 7-fold the UT-7 IC50 which is the exposure required for maximal efficacy in the wound model of mast cell expansion. PK extrapolation suggested that the antibody may likely clear 1 month after the last dose, but 9 months was selected as a conservative time point to assess recovery. Normal spermatogenesis was found in all dosed animals at 9 months demonstrating that use of a hSR-1 aIgG1-like molecule is useful as a male contraceptive.

Summary

Humanized anti-c-Kit aglycosylated IgG1 (hSR-1 aIgG1) antibody is a highly potent and specific antibody that is neutralizing in all cell based assays tested using proximal and distal read-outs of c-Kit signaling. Intrinsically it does not mediate c-Kit receptor internalization or phosphorylation as reported for the parent murine monoclonal SR-1 antibody. The selection of the aglycosylated IgG1 isotype over humanized IgG1, IgG2 and IgG4 isotypes would not have been predicted based on standard approaches. hSR-1 aIgG1 was chosen empirically via novel experimentation to show that it exhibited the appropriate pharmacological characteristics at the membrane c-Kit receptor, avoid agonist activity at c-Kit and on mast cells, lacking effector function and cell killing through bystander effects. This antibody showed good s.c. bioavailability and half-life, nonlinear PK and saturable target-mediated antibody elimination and mast cell depletion in monkeys. These data would predict a suitable human efficacious mast cell depleting dose.

The minimal efficacious dose of the parent mouse SR-1 monoclonal in the monkey wound PD model is <0.3 mg/Kg ($C_{trough}$>7-fold the cell IC50), and at slightly higher exposure ($C_{trough}$>800-fold the cell IC50) was efficacious as well in depleting basal skin, colon and lung mast cells. Similarly, exposure levels greater than >8000-fold the cell IC50 is required before qualitative impacts on hair pigmentation in newly regrown hair can be observed. Inhibition of hair pigmentation in newly growing hair has been reported with multi-kinase inhibitors and a c-Kit antibody in rodent and the hSR-1 aIgG1 may have utility in diseases associated with excessive melanocyte activity. The effect is reversible upon cessation of treatment. A sub-maximal effect on inhibition of spermatogenesis was shown at levels >7-fold the cell IC50, the exposure that conferred maximal efficacy in the wound PD model.

All of the above U.S. patents, U.S. patent application publications, U.S. patent applications, foreign patents, foreign patent applications and non patent publications referred to in this specification and/or listed in the Application Data Sheet, are incorporated herein by reference, in their entirety.

From the foregoing it will be appreciated that, although specific embodiments of the invention have been described herein for purposes of illustration, various modifications may be made without deviating from the spirit and scope of the invention.

What is claimed is:

1. A nucleic acid encoding a specific binding agent that binds c-Kit comprising an amino acid sequence selected from the group consisting of those set forth in SEQ ID NOS: 2, 4 and 6.

2. A nucleic acid encoding a specific binding agent that binds c-Kit comprising a nucleic acid sequence at least 90% identical to a nucleic acid selected from the group set forth in SEQ ID NOS: 1, 3 and 5.

3. A vector comprising the nucleic acid of claim 2.

4. A host cell comprising the vector of claim 3.

5. A method of producing a specific c-Kit binding agent comprising culturing a host cell of claim 4 such that the nucleic acid is expressed to produce the specific binding agent.

6. The method of claim 5, further comprising the step of recovering the specific binding agent from the host cell culture.

* * * * *